US007405050B2

(12) United States Patent
Lenz et al.

(10) Patent No.: US 7,405,050 B2
(45) Date of Patent: Jul. 29, 2008

(54) SMALL RNAS AND BACTERIAL STRAINS INVOLVED IN QUORUM SENSING

(75) Inventors: Derrick H. Lenz, Scotch Plains, NJ (US); Kenny C. Mok, San Diego, CA (US); Ned S. Wingreen, Princeton, NJ (US); Bonnie L. Bassler, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 457 days.

(21) Appl. No.: 11/104,705

(22) Filed: Apr. 12, 2005

(65) Prior Publication Data

US 2006/0057607 A1 Mar. 16, 2006

Related U.S. Application Data

(60) Provisional application No. 60/561,660, filed on Apr. 12, 2004.

(51) Int. Cl.
*G01N 33/53* (2006.01)
(52) U.S. Cl. ...................................... 435/7.1
(58) Field of Classification Search ................... 435/7.1
See application file for complete search history.

(56) References Cited

U.S. PATENT DOCUMENTS

| 6,559,176 | B1 | 5/2003 | Bassler et al. |
| 6,720,415 | B2 | 4/2004 | Bassler et al. |
| 6,780,890 | B2 | 8/2004 | Bassler et al. |
| 6,844,423 | B2 | 1/2005 | Bassler et al. |
| 6,864,067 | B2 | 3/2005 | Bassler et al. |

FOREIGN PATENT DOCUMENTS

| WO | WO 00/32152 A2 | 6/2000 |
| WO | WO 00/32152 A3 | 6/2000 |
| WO | WO 01/85773 A2 | 11/2001 |
| WO | WO 03/018046 A1 | 3/2003 |
| WO | WO 03/064592 A2 | 8/2003 |
| WO | WO 03/064592 A3 | 8/2003 |
| WO | WO 2004/101826 A2 | 11/2004 |
| WO | WO 2004/101826 A3 | 11/2004 |

OTHER PUBLICATIONS

Barrios, H. et al., "Compilation and analysis of the $\sigma^{54}$-dependent promoter sequences," Nucleic Acids Res. 27, 4305-4313 (1999).
Bassler, B. L. et al., "Intercellular signalling in *Vibrio harveyi*: sequence and function of genes regulating expression of luminescence," Mol. Microbiol. 9, 773-786 (1993).
Bassler, B. L. et al., "Multiple signalling systems controlling expression of luminescence in *Vibrio harveyi*: sequence and function of genes encoding a second sensory pathway," Mol. Microbiol. 13, 273-286 (1994).
Bassler, B. L. et al., "Sequence and function of LuxO, a negative regulator of luminescence in *Vibrio harveyi*," Mol. Microbiol. 12, 403-412 (1994).

Benson, A. K. et al., "The *Caulobacter crescentus* FlbD protein acts at *ftr* sequence elements both to activate and to repress transcription of cell cycle-regulated flagellar genes," Proc. Natl. Acad. Sci. 91, 4989-4993 (1994).
Cao, J. et al., "Purification and Structural Identification of an Autoinducer for the Luminescence System of *Vibrio harveyi*," J. Biol. Chem. 264, 21670-21676 (1989).
Chen, X. et al., "Structural identification of a bacterial quorum-sensing signal containing boron," Nature 415, 545-549 (2002).
Chen, C. et al., "Comparative Genome Analysis of *Vibrio vulnificus*, a Marine Pathogen," Genome Res. 13, 2577-2587 (2003).
Dombrecht, B. et al., "Prediction and overview of the RpoN-regulon in closely related species of the Rhizobiales," Genome Biol. 3. Published online Nov. 26, 2002. research0076.1-0076.11.
Freeman, J. A. et al., "A genetic analysis of the function of LuxO, a two-component response regulator involved in quorum sensing in *Vibrio harveyi*," Mol. Microbiol. 31, 665-677 (1999).
Freeman, J. A. et al., "Sequence and Function of LuxU: a Two-Component Phosphorelay Protein That Regulates Quorum Sensing in *Vibrio harveyi*," J. Bacteriol. 181, 899-806 (2000a).
Freeman, J. A. et al., "A genetic analysis of the functions of LuxN: a two-component hybrid sensor kinase that regulates quorum sensing in *Vibrio harveyi*," Mol. Microbiol. 35, 139-149 (2000).
Hammer, B. K. et al., "Quorum sensing controls biofilm formation in *Vibrio cholerae*," Mol. Microbiol. 50, 101-104 (2003).
Heidelberg, J. F. et al., "DNA sequence of both chromosomes of the cholera pathogen *Vibrio cholerae*," Nature 406, 477-483 (2000).
Henke, J. M. et al., "Quorum Sensing Regulates Type III Secretion in *Vibrio harveyi* and *Vibrio parahaemolyticus*," J. Bacteriol. 186, 3794-3805 (2004).
Henke, J. M. et al., "Three Parallel Quorum-Sensing Systems Regulate Gene Expression in *Vibrio harveyi*," J. Bacteriol. 186, 6902-6914.
Hertz, G. Z. et al., "Identifying DNA and protein patterns with statistically significant alignments of multiple sequences," Bioinformatics 15, 563-577 (1999).

(Continued)

*Primary Examiner*—Mark Navarro
(74) *Attorney, Agent, or Firm*—Mathews, Shepherd, McKay & Bruneau, P.A.

(57) ABSTRACT

Quorum-sensing bacteria communicate with extracellular signal molecules called autoinducers to allow community-wide synchronization of gene expression. The present invention relates to the identification the *Vibrio harveyi* and *Vibrio cholerae* protein Hfq as mediating interactions between small, regulatory RNAs (sRNAs) and specific messenger RNA (mRNA) targets. Accordingly, the present invention provides nucleic acids encoding the *Vibrio* sRNAs, strains having various deletions and mutations of one or more qrr genes encoding these sRNA as well as methods of identifying quorum-sensing regulators. Additionally, the invention relates to an isolated *V. harveyi* Hfq protein and conservative amino acid substitutions thereof as well as nucleic acids encoding those proteins, recombinant methods of producing those proteins and antibodies against those proteins.

9 Claims, 16 Drawing Sheets

OTHER PUBLICATIONS

Jobling, M. G. et al., "Characterization of *hapR*, a positive regulator of the *Vibrio cholerae* HA/protease gene *hap*, and its identification as a functional homologue of the *Vibrio harveyi luxR* gene," Mol. Microbiol. 26, 1023-1034 (1997).

Kovacikova, G. et al., "Regulation of virulence gene expression in *Vibrio cholerae* by quorum sensing: HapR functions at the *aphA* promoter," Mol. Microbiol. 46, 1135-1147 (2002).

Lenz, D. H. et al., "The small RNA chaperone Hfq and multiple small RNAs control quorum sensing in *Vibrio harveyi* and *Vibrio cholerae*," Cell 18, 69-82 (2004).

Lilley, B. N. et al., "Regulation of quorum sensing in *Vibrio harveyi* by *LuxO* and Sigma-54," Mol. Microbiol. 36, 940-954 (2000).

Makino, K. et al., "Genome sequence of *Vibrio parahaemolyticus*: a pathogenic mechanism distinct from that of *V cholerae*," Lancet 361, 743-749 (2003).

Martin, M. et al., "Identification of a Locus Controlling Expression of Luminescence Genes in *Vibrio harveyi*," J. Bacteriol. 171, 2406-2414 (1989).

Masse, E. et. al., "Coupled degradation of a small regulatory RNA and its mRNA targets in *Escherichia coli*," Genes Dev. 17, 2374-2383 (2003).

Miller, M. B. et al., "Quorum Sensing in Bacteria," Ann. Rev. Microbiol. 55,165-199 (2001).

Miller, M. B. et al., "Parallel Quorum Sensing Systems Converge to Regulate Virulence in *Vibrio cholerae*," Cell 110, 303-314 (2002).

Miller, S. T. et al., "*Salmonella typhimurium* recognizes a chemically distinct form of the bacterial quorum-sensing signal Al-2," Mol. Cell 15, 677-687 (2004).

Miyamoto, C. M. et al., "Proximal and distal sites bind LuxR independently and active expression of the *Vibrio harveyi lux* operon," Mol. Microbiol. 14, 255-262 (1994).

Mok, K. C. et al., "*Vibrio harveyi* quorum sensing: a coincidence detector for two autoinducers controls gene expression," EMBO J. 22, 870-881 (2003).

North, A. K. et al., "Repressor Forms of the Enhancer-binding Protein NtrC: Some Fail in Coupling ATP Hydrolysis to Open Complex Formation by $\sigma^{54}$-Holoenzyme," J. Mol. Biol. 260, 317-331 (1996).

Paulsson, J. et al., "Noise in a minimal regulatory network: plasmid copy number control," Q. Rev. Biophys. 34, 1-59 (2001).

Reitze, L. J. et al., "Expression of *glnA* in *Escherichia coli* is regulated at tandem promoters," Proc. Natl. Acad. Sci. USA 82,1979-1983 (1985).

Showalter, R. E. et al., "Cloning and Nucleotide Sequence of *luxR*, a Regulatory Gene Controlling Bioluminescence in *Vibrio harveyi*," J. Bacteriol. 172, 2946-2954 (1990).

Surette, M. G. et al., "Quorum sensing in *Escherichia coli, Salmonella typhimurium*, and *Vibrio harveyi*: A new family of genes responsible for autoinducer production," Proc. Natl. Acad. Sci. USA 96, 1639-1644 (1999).

Vance, R. E. et al., "A Constitutively Active Variant of the Quorum-Sensing Regulator LuxO Affects Protease Production and Biofilm Formation in *Vibrio cholerae*," Infect. Immun. 71, 2571-2576 (2003).

van Helden, J. et al., "Regulatory Sequence Analysis Tools," Nucleic Acids Res. 31, 3593-3596 (2003).

Wingrove, J. A. et al., "A $\sigma^{54}$ transcriptional activator also functions as a pole-specific repressor in *Caulobacter*," Genes Dev. 8, 1839-1852 (1994).

Wu, J. et al., "Regulation of the *Caulobacter* flageller gene hierarchy; not just for motility," Mol. Microbiol. 24, 233-239 (1997).

Zhu, J. et al., "Quorum Sensing-Dependent Biofilms Enhance Colonizatioin in *Vibrio cholerae*," Dev. Cell 5, 647-656 (2003).

Zhu, J. et al., "Quorum-sensing regulators control virulence gene expression in *Vibrio cholerae*," Proc. Natl. Acad. Sci. 99, 3129-3134 (2002).

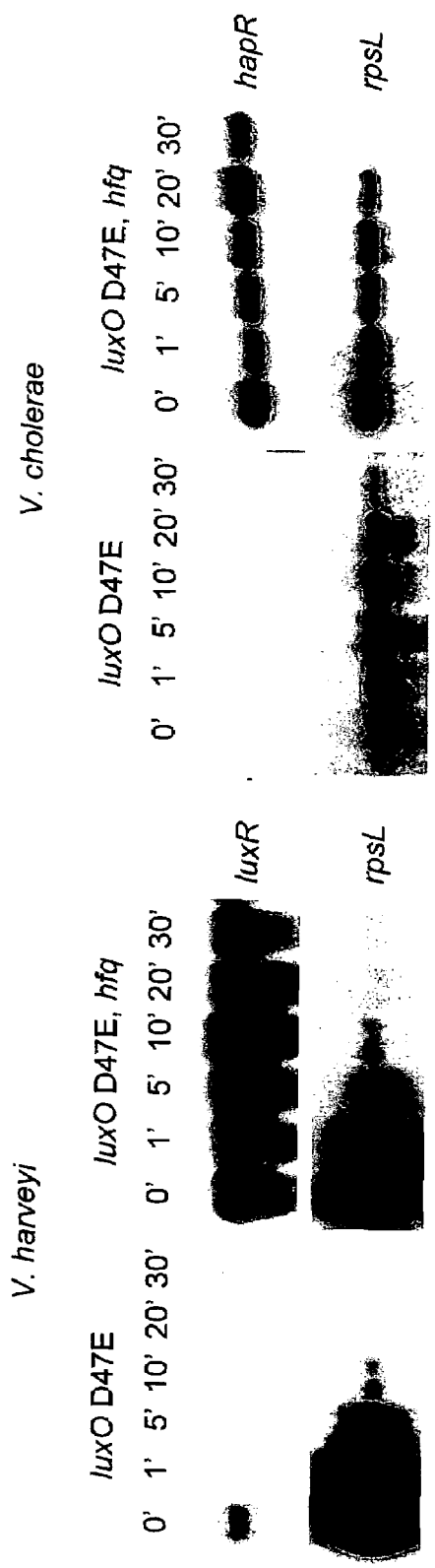
FIG. 3A
FIG. 3B

```
                                                                                              +1
hapR            CAUAGGGGUAUAUCCUUGCCAAUUGAGCAUUUGCUCUAAUGAUAUUUGUUAUUUGCUACUUAAAGCC
V.cholerae Qrr1 .........GGGUCACCUAGCCAACUGACGUUGUUAGUUGAA.........................
V.cholerae Qrr2 .........GGGUCACCUAGCCAACUGACGUUGUUAGUGAA..........................
V.cholerae Qrr3 .........GGGUCACCUAGCCAACUGACGUUGUUAGUGAA..........................
V.cholerae Qrr4 .........GGGUCACCUAGCCAACUGACGUUGUUAGUGAA..........................
                Start    RBS
```

FIG.5C

```
                                                                                              +1
luxR             CAUAAUCCAUUUUCCUUGCCAUUGA.GUUGAUAUUUGGGGAUAGUCCCUAAUGAUUAUUUAAUAGUUGCUUAAAGCA
V.harveyi Qrr1   ..........GGGUCACCUAUCUGAACUGACGUUGUUAGUGAA.................................
                 Start    RBS
```

FIG.5D

SMALL RNAS AND BACTERIAL STRAINS INVOLVED IN QUORUM SENSING

This application claims benefit under 35 U.S.C. § 119(e) of U.S. Provisional Ser. No. 60/561,660, filed Apr. 12, 2004, which is incorporated herein by reference.

GOVERNMENT INTERESTS

This invention was funded in part through grants from the National Science Foundation, Office of Naval Research and the National Institutes of Health. Therefore, the federal government has certain rights in this invention.

FIELD OF THE INVENTION

Quorum-sensing bacteria communicate with extracellular signal molecules called autoinducers to allow community-wide synchronization of gene expression. The present invention relates to the identification the *Vibrio harveyi* and *Vibrio cholerae* protein Hfq as mediating interactions between small, regulatory RNAs (sRNAs) and specific messenger RNA (mRNA) targets. Accordingly, the present invention provides nucleic acids encoding the *Vibrio* sRNAs, strains having various deletions and mutations of one or more qrr genes encoding these sRNA as well as methods of identifying quorum-sensing regulators. Additionally, the invention relates to an isolated *V. harveyi* Hfq protein and conservative amino acid substitutions thereof as well as nucleic acids encoding those proteins, recombinant methods of producing those proteins and antibodies against those proteins.

BACKGROUND OF THE INVENTION

Quorum sensing is a process of cell-to-cell communication that bacteria use to assess their population density in order to coordinate the gene expression of the community (Miller et al., 2001). Quorum sensing requires the production, secretion, and detection of extra-cellular signal molecules termed autoinducers. Diverse behaviors are controlled by quorum sensing, but, typically, these behaviors are ones that would be ineffective if only a small group of cells carried them out. Often, bacteria produce and detect multiple autoinducers, some of which are used for intraspecies communication, while others promote interspecies communication (Federle et al., 2003; Fuqua et al., 2001; Xavier et al., 2003).

The marine bacterium *Vibrio harveyi* produces and detects two autoinducers, AI-1 and AI-2, and these signals control the expression of multiple genes, including those for bioluminescence (luciferase) (Bassler et al., 1993, 1994a; Cao et al., 1989; Chen et al., 2002b), siderophore production (Lilley et al., 2000), colony morphology, metalloprotease production (Mok et al., 2003), and type III secretion (Henke et al., 2004).

In *V. harveyi*, AI-1 and AI-2 are produced by the synthases LuxM and LuxS, respectively (Bassler et al., 1993; Surette et al., 1999). LuxN detects AI-1, and LuxPQ detects AI-2 (FIG. 1A) (Bassler et al., 1993, 1994a; Chen et al., 2002b; Freeman et al., 2000b). LuxN and LuxQ are membrane bound, two-component hybrid sensor-kinase proteins. LuxP, which binds AI-2 in the periplasm, is required with LuxQ for the response to AI-2 (Bassler et al., 1994a; Chen et al., 2002b). Sensory information from both systems converges at the phosphorelay protein LuxU, and LuxU transmits the signal to the response regulator LuxO (Bassler et al., 1994b; Freeman et al., 1999, 2000a). A transcriptional activator called LuxR is also required for expression of lux (the operon encoding the bioluminescence genes in *V. harveyi*) and other quorum sensing-controlled genes (Henke et al., 2004; Martin et al., 1989; Miyamoto et al., 1994; Showalter et al., 1990).

The human pathogen *Vibrio cholerae* possesses quorum-sensing systems analogous to the two described above for *V. harveyi* (Miller et al., 2002). The *V. cholerae* autoinducers CAI-1 and AI-2 are synthesized by CqsA and LuxS and detected by CqsS and LuxPQ, respectively (FIG. 1B). *V. cholerae* has an additional system (System 3; Miller et al., 2002). Sensory information from all three systems converges at LuxO. The *V. cholerae* LuxR homolog is called HapR (Jobling et al., 1997). Quorum sensing controls virulence and biofilm formation in *V. cholerae* (Hammer et al., 2003; Kovacikova et al., 2002; Miller et al., 2002; Vance et al., 2003; Zhu et al., 2003; Zhu et al., 2002).

The *V. harveyi* and *V. cholerae* quorum-sensing circuits operate similarly (Miller et al., 2002). At low cell density, i.e., in the absence of autoinducers, the sensors act as kinases and transfer phosphate via LuxU to LuxO. LuxO-phosphate (LuxO-P) is active and negatively regulates lux. At high cell density, i.e., when the autoinducers are present, the sensors act as phosphatases. Phosphate flow through the circuit is reversed, resulting in dephosphorylation and inactivation of LuxO (Freeman et al., 1999, 2000a; Freeman et al., 2000b). Under this condition, the transcriptional regulators LuxR in *V. harveyi* and HapR in *V. cholerae* bind the lux promoter and activate transcription (FIG. 1).

LuxO-P-mediated repression of lux is indirect (Lilley et al., 2000). LuxO is homologous to members of the NtrC family of response regulators, which can act either as transcriptional activators or repressors. Those that are activators require the alternative sigma factor σ54 for function, while those that are repressors do not (Benson et al., 1994; North et al., 1996; Reitzer et al., 1985; Wingrove et al., 1994; Wu et al., 1997). LuxO is a member of the activator class of NtrC homologs. It has been hypothesized that, at low cell density, LuxO-P activates the expression of a repressor that controls the downstream target genes.

The present invention relates to the discovery that multiple, redundant small regulatory RNAs (sRNAs), together with the sRNA binding protein Hfq, fulfill this repressor role. Specifically, at low cell density, the Hfq-sRNA repressor complexes destabilize the *V. harveyi* luxR and *V. cholerae* hapR mRNAs (FIG. 1).

SUMMARY OF THE INVENTION

One aspect of the present invention relates to sRNAs encoded by the qrr genes of *Vibrio* species, *Vibrio* strains containing various deletions of those genes and method to use those strains to identify regulators of quorum sensing.

In particular, one embodiment provides an isolated nucleic acid encoding an sRNA from a *Vibrio* species. Such sRNAs interact with the Hfq protein from *V. cholerae* (or its equivalent in that species) and are sufficiently complementary to stably bind to a hapR mRNA (e.g., in *V. cholerae* or its equivalent in the species such as luxR mRNA in *V. harveyi*) and to thereby regulate quorum sensing. Each qrr gene is under control of the transcription factor sigma 54 ($\sigma^{54}$) and LuxO (or the relevant equivalent) and has a Rho-independent terminator. In *V. cholerae*, the qrr genes are located in the intergenic regions between annotated genes. The same is true for the qrr genes from *V. parahaemolyticus* and *V. vulnificus* and appears to be the case for *V. harveyi*. The sRNA is from any *Vibrio* species containing qrr genes, and is preferably from *V. cholerae*, *V. parahaemolyticus*, *V. vulnificus* or *V.* harveyi. *V. cholerae* has 4 qrr genes (qrr1-qrr4) whereas *V. parahaemolyticus*, *V. vulnificus* and *V. harveyi* each have five qrr genes (qrr1-qrr5).

The nucleotide sequences for the qrr genes of the above *Vibrios* is provided, in the case of the DNA, in SEQ ID NOs. 1-19 and in the case of the RNA, in SEQ ID NOS. 20-38. Additionally, the invention provides nucleic acids that encode the sRNAs of the invention and that hybridizes to these sequences under stringent conditions.

Another aspect of the invention relates to expression vectors that express one or more sRNAs of claim 1 as well as cells that comprise those vectors and that can be used to produce the one or more sRNAs. For example, sRNA can be produced by culturing cells of the invention for a time and under conditions sufficient to express an sRNA and the sRNA can be recovered by conventional means.

Yet another aspect of the invention provides isolated *Vibrio* strains that have a deletion or mutation of one or more qrr genes. Such strains are useful, among other things, to analyze regulation of quorum sensing and to identify regulators of quorum sensing. These strains are from any *Vibrio* species and, preferably are from *V. cholerae, V. parahaemolyticus, V. vulnificus* or *V. harveyi*. Any of these strains can have one or more deletions or mutations of any other gene involved in any of the quorum sensing pathways, see, e.g., FIG. 1. Examples of *V. cholerae* strains having deletions of three of the four qrr genes include, but are not limited to, DL2998, DL2996, DL2955 or DL2997. Examples of *V. cholerae* strains having deletions of all four qrr genes, include, but are not limited to, DL2956, DL3024, DL2953 or DL3020.

Still another aspect of the invention relates to an isolated *V. harveyi* Hfq protein and conservative amino acid substitutions thereof as well as nucleic acids encoding those proteins, recombinant methods of producing those proteins and antibodies against those proteins.

A further aspect of the invention provides a method of identifying a quorum-sensing regulator by contacting *Vibrio* cells that have at least one inactivated qrr gene with a test compound and assaying a quorum-sensing response to the compound, and with appropriate controls, thereby identify or determine that the compound regulates quorum sensing. This method can readily be adapted for high throughput screening of test compounds. In a preferred embodiment the *Vibrio* cells have no more than one active qrr gene. Quorum-sensing responses can be measured by many different techniques, including cell density-dependent changes in light production or in a reporter system. Reporter systems are well known in the art and can be used in conjunction with the lux promoter or other quorum-sensing promoter.

When measuring light production in cells that have a single active qrr gene, the method identifies activators of quorum sensing. When measuring light production in cells with no active qrr genes, the method identifies inactivators of quorum sensing. While measurement of light production is preferred, this method can be adapted to use any other measurable parameters indicative of quorum sensing to identify the desired regulators. For measuring light production, the compounds can be tested on *V. harveyi* strains, which are naturally bioluminescent or on any *Vibrio* strain that has been engineered to carry a lux operon, usually the *V. harveyi* lux operon. Such strains include, for example, *V. cholerae, V. parahaemolyticus, V. vulnificus, V. fisherii* and *V. anguillarum*.

BRIEF DESCRIPTION OF THE DRAWINGS

FIG. 1 graphically illustrates models of the *V. harveyi* and *V. cholerae* quorum-sensing circuits.

In FIGS. 2B and 2C, the dotted lines represent the limit of detection for light.

FIG. 3A presents non-steady state Northern blots which show Hfq regulates the expression of luxR and hapR posttranscriptionally. luxR/hapR transcript stability was analyzed in the following strains: *V. harveyi* JAF548 (luxO D47E) and BNL211 (luxO D47E, hfq::Mini-MulacZ) (left four panels); and *V. cholerae* BH38 (luxO D47E) and DL2146 (luxO D47E, Δhfq) (right four panels).

FIG. 3B shows Western blots on lysates for the left panel of *V. harveyi* BB120 (WT), JAF548 (luxO D47E), BNL258 (hfq::Tn5lacZ), BNL211 (luxO D47E, hfq::Mini-MulacZ), and for the right panel of *V. cholerae* C6706str2 (WT), BH38 (luxO D47E), DL2066 (Δhfq), DL2146 (luxO D47E, Δhfq) to measure LuxR and HapR protein, respectively.

FIG. 4 presents bar graphs demonstrating that LuxO-P and Hfq regulate hapR posttranscriptionally.

FIG. 5A shows a multiple sequence alignment of the qrr genes encoding the sRNAs identified in *V. cholerae, V. parahaemolyticus, V. vulnificus*, and *V. harveyi*. Annotations for the genes flanking each sRNA are given in the brackets. Numbering of sRNAs is based on orthology of flanking genes. Nucleotides in black indicate perfect alignment. The putative σ$^{54}$ binding site is marked as −12 and −24, the predicted start of transcription is labeled as +1, and the terminator is noted by the line over the sequence.

FIG. 5C presents an alignment of the complement of the hapR UTR (shown in the 3' to 5' direction; SEQ ID NO. 44) with a portion of the Qrr sRNAs identified in *V. cholerae* (shown in the 5' to 3' direction). FIG. 5D presents a similar alignment of the complement of the luxR UTR (SEQ ID NO. 45) with a portion of sRNA Qrr1 identified in *V. harveyi*. In FIGS. 5C and 5D, the translational start site (Start), the ribosome binding site (RBS), and the transcriptional start site (+1) are indicated. FIGS. 5A, 5C and 5D were produced using CLUSTALW (Thompson et al., 1994) and ESPript (Gouet et al., 1999).

FIG. 7A shows a plot of bioluminescence versus cell density for *V. cholerae* MM227 (WT, open squares), MM349 (ΔluxO, open diamonds), DL2998 (Δqrr2, Δqrr3, Δqrr4, closed squares), DL2996 (Δqrr1, Δqrr3, Δqrr4, closed diamonds), DL2955 (Δqrr1, Δqrr2, Δqrr4, closed triangles), DL2997 (Δqrr1, Δqrr2, Δqrr3, closed circles), DL2956 (Δqrr1, Δqrr2, Δqrr3, Δqrr4, open circles).

Figure 1A:
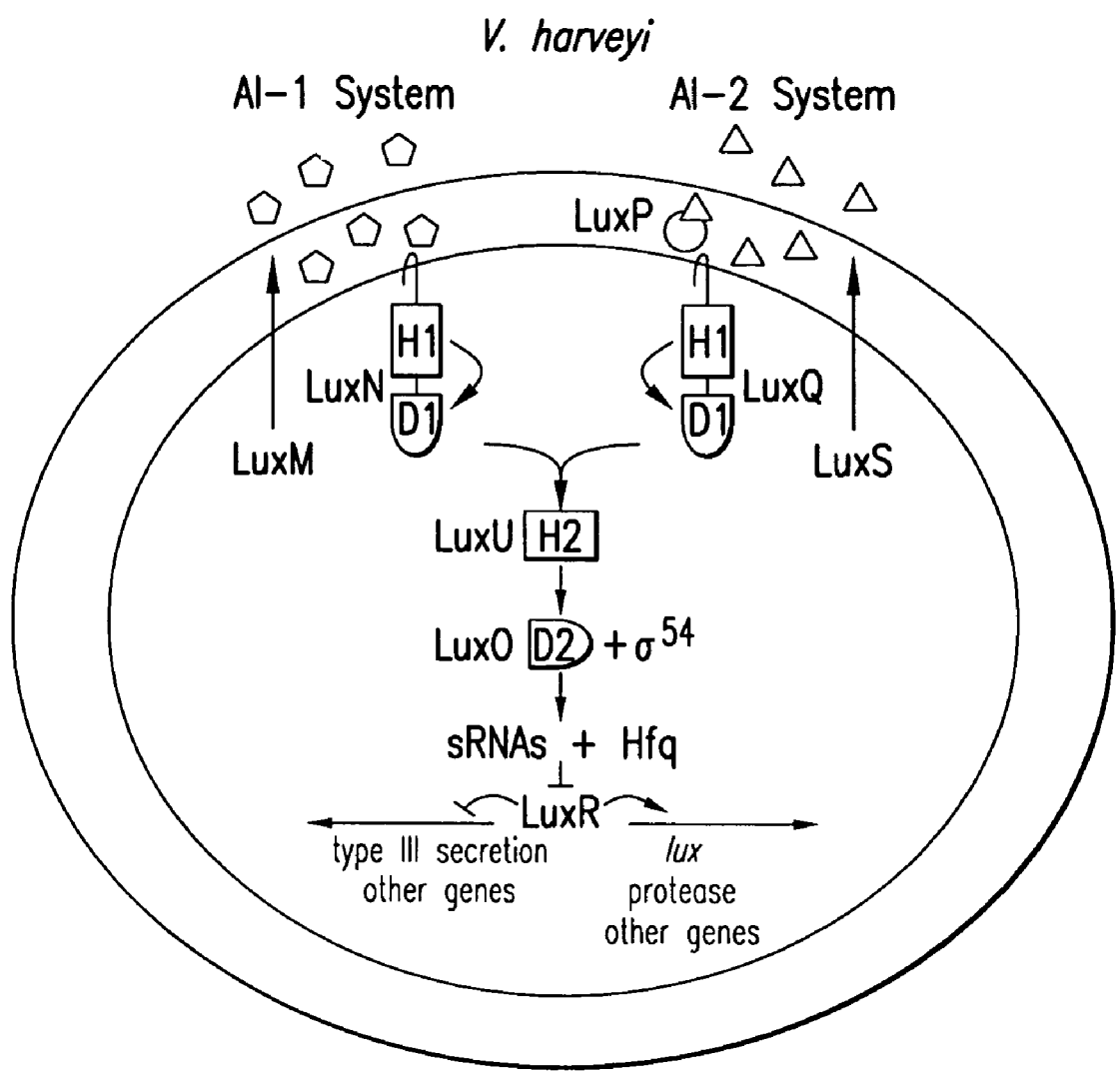
FIG. 1A shows that two quorum-sensing systems function in parallel to regulate gene expression in *V. harveyi*. Pentagons and triangles represent AI-1 and AI-2, respectively.
Figure 1B:
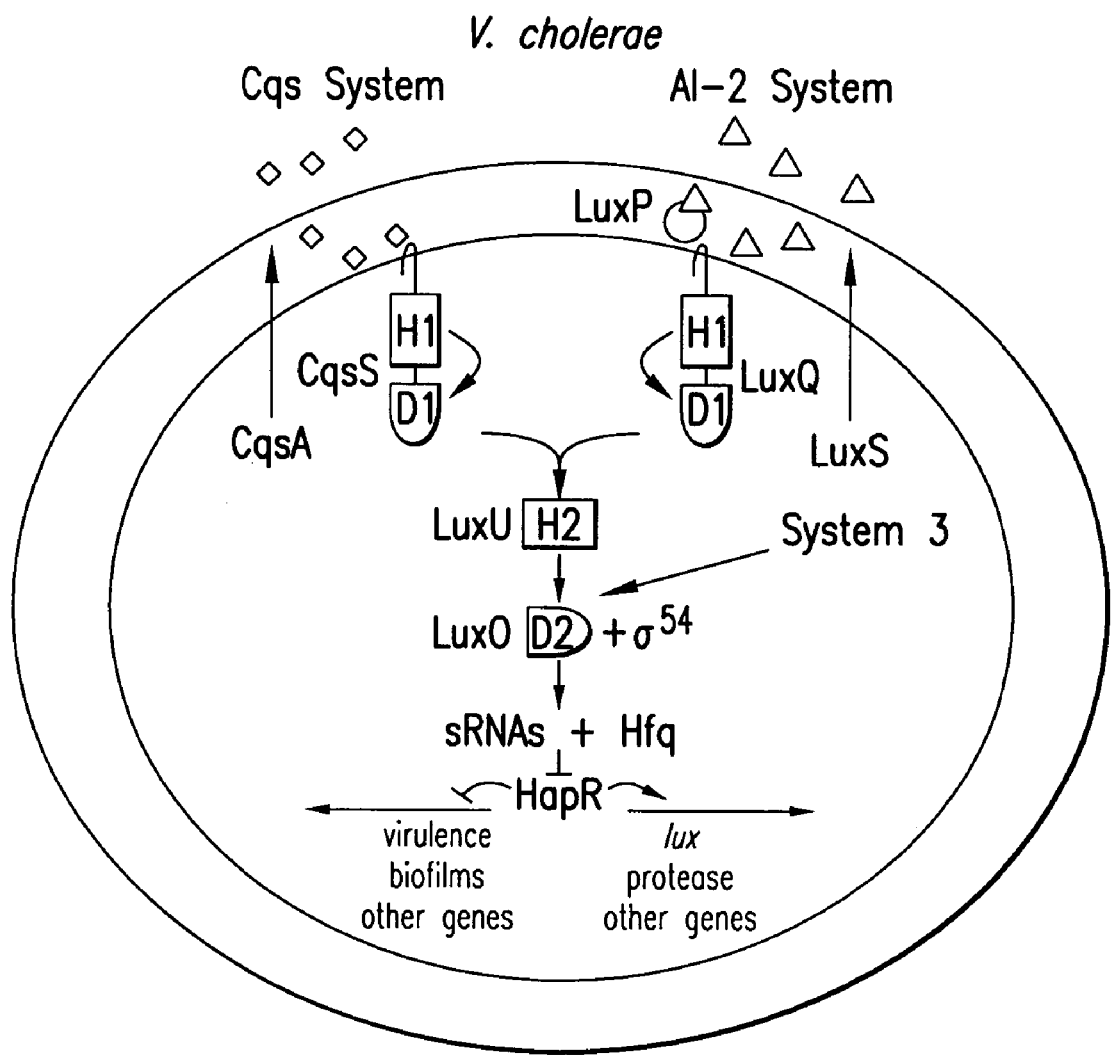
FIG. 1B shows that three quorum-sensing systems function in parallel to regulate gene expression in *V. cholerae*. The functions making up the third circuit (denoted System 3) remain to be identified. Diamonds and triangles represent CAI-1 and AI-2, respectively. In both circuits, phosphate flows in the direction indicated by the arrows at low cell density and in the opposite direction at high cell density.

DETAILED DESCRIPTION OF THE INVENTION sRNA Nucleic Acids, qrr Genes and Uses

The decision to transition from acting alone to participating in a group activity is a significant one for bacteria. In Vibrios, sophisticated regulatory devices are located at different positions in the quorum-sensing signal-transduction relay to ensure that this decision occurs under the appropriate set of circumstances and with high fidelity. Previously, it was shown that a coincidence detector regulates entry into high cell density mode: the simultaneous presence of multiple autoinducers is required to reverse the direction of phospho-flow through the system and thus to initiate the transition from the individualistic to the group lifestyle (Mok et al., 2003). The coincidence-detection scheme likely protects the quorum-sensing circuit from molecules in the environment that resemble the bona fide autoinducers. This invention relates to the discovery that an ultrasensitive switch involving multiple sRNAs exists to make the commitment step into quorum-sensing mode definitive. This transition is not graded but rather acts as an on/off switch, which turns off behaviors that are useful when carried out alone and turns on behaviors that are productive when carried out as a community.

Accordingly, one aspect of the invention relates to isolated nucleic acids which encode one or more sRNAs involved in quorum sensing regulation in a *Vibrio* species, wherein the sRNA interacts with a *Vibrio cholerae* Hfq protein or with the corresponding protein from the particular *Vibrio* species; the sRNA has a sequence sufficiently complementary to stably bind to a *V. cholerae* hapR mRNA or to the corresponding mRNA from the particular *Vibrio* species. The sRNA as encoded in the *Vibrio* genome is found in an intergenic region and is under transcriptional control of a *V. cholerae* transcription factor sigma 54 ($\sigma^{54}$) or the corresponding transcription factor from the particular *Vibrio* species as well as under transcriptional control of a *V. cholerae* LuxO protein or the corresponding protein from the particular *Vibrio* species. The sRNA gene is followed by a Rho-independent terminator.

Preferred *Vibrio* species include but are not limited to, *V. cholerae*, *V. parahaemolyticus*, *V. vulnificus* or *V. harveyi*. Other *Vibrio* species include *V. fluvialis*, *V. fisherii*, *V. hollisae*, *V. alginolyticus*, *V. furnissii*, *V. metschnikovii*, *V. cincinnatiensis*, *V. damsela*, *V. carchariae*, *V. anguillarum*, *V. damsela*, and *V. carchariae*.

The nucleic acids of the invention are composed of RNA, DNA, stabilized RNA, stabilized DNA or RNA or DNA having unusual or bases or sugars, provided that such molecules function as sRNAs in quorum sensing in accordance with the instant invention. Any of these molecules can be made either recombinantly or synthetically by techniques known to those of ordinary skill in the art. Stabilized RNA and DNA include molecules that have substituted phosphate backbones, such as phosphorothioate groups, or other linkages or moieties known to stabilize RNA and DNA and prevent its degradation.

*V. parahaemolyticus*, *V. vulnificus* and *V. harveyi* each have five sRNAs. These sRNAs are encoded by the qrr1-qrr5 genes. *V. cholerae* has four qrr genes, namely qrr1-qrr4. In one embodiment of the invention, the nucleic acids of the invention comprise any one of the sequences provided in SEQ ID NOS. 1-19 (in the case of DNA) or 20-38 (in the case of RNA) or the complement of any of these sequences. Each of these sequences represent the sRNA encoded by a qrr from one of the foregoing *Vibrio* species.

In another embodiment of the invention, the nucleic acid of the invention consists essentially of an sRNA sequence. In addition, the nucleic acids of the invention, include isolated nucleic acids which hybridize to those encoded in SEQ ID NOS. 1-38 under stringent conditions, and preferably under highly stringent conditions. For example, such nucleic acids are identified by using hybridization and washing conditions of the desired high stringency, e.g., as described in Sambrook et al. (1989) Such nucleic acids can be isolated, cloned and/or sequenced if desired. In a preferred embodiment, the stringent hybridization conditions include a step of hybridizing in 6×SSC at about 45° C. followed by one or more washes in 0.1×SSC/0.2% SDS at about 68° C., or equivalently stringent hybridization conditions.

As used herein, "isolated nucleic acid" means (1) a DNA molecule that is separated from sequences with which it is immediately contiguous (in the 5' and 3' directions) in the naturally occurring genome of the organism from which it was derived or (2) a DNA molecule with the indicated sequence but which has undergone some degree of purification relative to the genome and may retains some number of immediately contiguous genomic sequences. For example, such molecules include those present on an isolated restriction fragment or such molecules obtained by PCR amplification. DNA can be isolated and purified to any degree using methods well known in the art.

In accordance with the invention, the "isolated nucleic acid" may be inserted into or itself comprise a vector, such as a plasmid or virus vector, or be integrated into the genomic DNA of a prokaryote or eukaryote. With respect to RNA molecules of the invention, the term "isolated nucleic acid" primarily refers to an RNA molecule encoded by an isolated DNA molecule as defined above. But also includes RNA that has been isolated from a cellular source or RNA that has been chemically synthesized (and obtained at any level of purity). In these cases, the RNA molecule has been sufficiently separated from RNA molecules with which it would be associated in its natural state (i.e., in cells or tissues), such that it exists in a purified pure form, e.g., that the RNA is enriched in the mixture relative to its abundance as naturally produced.

In a preferred embodiment, the isolated nucleic acid is an expression vector and has the sRNA sequence operably linked to a promoter or other regulatory sequences to control expression thereof. Expression vectors can encode one or more sRNAs and these can be coordinately or individually expressed, e.g., using one promoter or multiple promoters. Useful promoters and regulatory sequences for any of the expression vectors of the are well known to those of skill in the art.

Expression vectors are useful for any one of the following purposes: propagation of the sRNA, purification of the sRNA, or delivery and expression of the sRNA in a subject. Expression vectors can be used for any cell type, including bacterial, yeast, insect and mammalian systems, and include all types of vectors including viral vectors. Methods of making and using expression vectors, as well as selecting the appropriate host cell system are well known to those of skill in the art. Well-known promoters can be present, such as the lactose promoter system, a tryptophan (Trp) promoter system, a beta-lactamase promoter system, an arabinose-inducible promoter or a promoter system from phage lambda. The promoters typically control expression, optionally with an operator sequence and have ribosome binding site sequences for example, for initiating and completing transcription and translation. Among vectors preferred for use in bacteria include pQE70, pQE60 and pQE9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Any expression vector is contemplated.

Vibrio Strains and Methods of Use

Another aspect of the present invention provides Vibrio strains having a deletion or mutation of one or more qrr genes. With qrr genes identified and sequenced, those of skill in the art can readily delete or mutate one or more qrr genes in a Vibrio strain of any genetic background. In a preferred aspect, any other gene or allele involved in quorum sensing can be present or absent in these strains. Examples of such other genes, include but are not limited to luxO, luxS, luxO D47E (the "locked" strain), hfq and the like.

Mutants can be made by PCR mutagenesis, site-directed mutagenesis, allele replacement (Bassler et al. 1993) or any other methods known to those of skill in the art. V. harveyi deletions can be constructed, for example, using the method of Datsenko et al. (2000). As another example, in-frame deletions can be constructed by the method of Skorupski et al. (1996). The qrr gene deletions or mutations are introduced, constructed or are otherwise selected in any Vibrio species, including those listed elsewhere herein. The preferred species are V. cholerae, V. parahaemolyticus, V. vulnificus and/or V. harveyi.

Any number of qrr genes can be deleted or mutated in the strains of the invention, i.e., single, double, triple, quadruple and quintuple (if applicable) mutants can be constructed. Examples of V. cholerae triple mutant strains include DL2998 (Δqrr2, Δqrr3, Δqrr4), DL2996 (Δqrr1, Δqrr3, Δqrr4) and DL2955 (Δqrr1, Δqrr2, Δqrr4), DL2997 (Δqrr1, Δqrr2, Δqrr3). Examples of V. cholerae quadruple mutants, i.e., having no active qrr genes, include DL2956 (Δqrr1, Δqrr2, Δqrr3, Δqrr4), DL3024 (luxO D47E, Δqrr1, Δqrr2, Δqrr3, Δqrr4), DL2953 (Δqrr1, Δqrr2, Δqrr3, Δqrr4) and DL3020 (luxO D47E, Δqrr1, Δqrr2, Δqrr3, Δqrr4).

Such strains are useful in methods for identifying regulators of quorum sensing including, but not limited to, methods of identifying a quorum-sensing regulator by (a) contacting Vibrio cells having at least one inactive qrr gene with a test compound; (b) assaying a quorum sensing response of those cells to the test compound; and comparing those results with appropriate controls to determine whether or not the test compound is a quorum-sensing regulator. In preferred embodiments, the Vibrio strains have no more than one active qrr gene or no active qrr genes.

Assays for quorum-sensing responses can be measured by many different techniques and are well known in the art. For example, in a preferred method, the assay measures cell density-dependent changes in light production or in a reporter system. Assays can also measure expression of virulence genes, biofilm formation or expression of any other gene or gene product under control of the quorum sensing system.

The general use of reporter systems are well known to those of skill in the art. In the present assays, reporter systems can conveniently be used in conjunction with the lux promoter or another quorum-sensing promoter. In one set of preferred embodiments, the reporter system comprises the V. harveyi lux operon, a lux promoter operably linked to a reporter molecule or a quorum-sensing promoter operably linked to a reporter molecule. Any reporter molecule can be used, including those adaptable to high throughput screening techniques. Examples of reporter molecules include, but are not limited to, β-galactosidase, a green fluorescent protein (GFP) or any fluorescent variant derivative thereof, a luciferase, chloramphenicol acetyl transferase (CAT), β-glucuronidase (GUS), alkaline phosphatase and horseradish peroxidase. The majority of these reporters are commercially available. In a preferred embodiment, the Vibrio cells are V. cholerae comprising a lux operon or are V. harveyi. Such assays can also be conducted with any naturally bioluminescent Vibrio. By measuring bioluminescence, this assay can be readily adapted to high through put screening methods.

When the Vibrio cells have one active qrr gene, this method is useful to identify activators of quorum sensing. when the Vibrio cells have no active qrr gene, this method is useful to identify inactivators of quorum sensing.

The quorum-sensing regulators identified by the above method can be used to promote or impede biofilm formation as well as to control virulence gene expression in pathogenic *Vibrio* species. Likewise, such regulators or their analogs, can be useful to control gene expression for systems influenced by quorum sensing in other bacterial species such as *Pseudomonas phosphoreum, Yersinia enterocolitica, E. coli, S. typhimurium, Salmonella typhi, Haemophilus influenzae, Helicobacter pylori, Bacillus subtilis, Borrelia burgfdorferi, Neisseria meningitidis, Neisseria gonorrhoeae, Yersinia pestis, Campylobacter jejuni, Deinococcus radiodurans, Mycobacterium tuberculosis, Enterococcus faecalis, Streptococcus pneumoniae, Streptococcus pyogenes* and *Staphylococcus aureus*.

Hfq Nucleic Acids, Proteins and Antibodies

In another embodiment, the invention is directed to isolated nucleic acids encoding a *V. harveyi* or *V. cholerae* Hfq protein comprising an amino acid sequence of SEQ ID NOS. 39 and 41, respectively, conservative amino acid substitutions therein as well as those proteins and isolated antibodies specific for those proteins.

The hfq nucleic acids of the invention can be produced recombinantly (e.g., by PCR cloning) or chemically synthesized. The nucleotide sequences for the coding regions of the *V. harveyi* or *V. cholerae* hfq genes are shown in SEQ ID NOS. 40 and 42, respectively.

Hfq nucleic acids of the invention, or fragments thereof, may be used as probes for hfq genes in (1) in situ hybridization; (2) Southern hybridization (3) Northern hybridization; and (4) assorted amplification reactions such as polymerase chain reactions (PCR). They may also be used as probes to identify related genes from other bacteria, including other *Vibrio* species.

Hfq nucleic acids may further be used to produce large quantities of substantially pure encoded protein, or selected portions thereof, using techniques known in the art. In this regard, the cloned genes inserted into expression vectors can be used to make large quantities of the molecule itself in a recombinant host such as *E. coli* DH5α. Large quantities of Hfq can be made through use of the cloned gene in an expression vector, and thereafter used in library screens for potential inhibitors targets in bioluminescence assays.

Purified Hfq, or fragments thereof, may be used to produce antibodies that also may serve as sensitive detection reagents for those proteins in cultured cells. Recombinant techniques enable expression of fusion proteins containing part or all of Hfq. The full length protein or fragments of the protein may be used to advantage to generate an array of antibodies specific for various epitopes of the protein, thereby providing even greater sensitivity for detection of the protein. Other uses of Hfq include overproduction to make a quantity sufficient for crystallization. Knowledge of the Hfq crystal structure would enable determination of Hfq sRNA binding site, and could therefore be used for computer-aided design of regulators of quorum sensing and for rational drug design.

Antibodies can be polyclonal, monoclonal, chimeric, humanized, or fragments thereof such as Fab, Fc, single chain Fvs and the like. Methods of making all of the foregoing are well known in the art. Such antibodies can be raised using the intact Hfq as the immunogen or any fragment thereof large enough to confer Hfq-specificity to the resultant antibodies.

Antibodies specific for Hfq may be used in a variety of assays designed to detect and quantitate the protein. Such assays include, but are not limited to: (1) flow cytometric analysis; (2) immunochemical localization of Hfq in cells; and (3) immunoblot analysis (e.g., dot blot, Western blot) of extracts from various cells and tissues. Additionally, as described above, antibodies can be used for purification of the proteins (e.g., affinity column purification, immunoprecipitation).

Pharmaceutical Preparations

Quorum sensing regulators can be formulated as pharmaceutical compositions comprising one or more of those molecules together with a pharmaceutically acceptable carrier. Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers are described in Gennaro et al., (1995). In addition to the pharmacologically active agent, the compositions can contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds, as appropriate in oily injection suspensions may be administered. Suitable lipophilic solvents or vehicles include fatty oils, for example, sesame oil or synthetic fatty acid esters, for example, ethyl oleate or triglycerides. Aqueous injection suspensions can contain substances which increase the viscosity of the suspension include, for example, sodium carboxymethyl cellulose, sorbitol, and dextran. Optionally, the suspension can also contain stabilizers. Liposomes can also be used to encapsulate the agent for delivery into the cell.

The pharmaceutical formulation for systemic administration according to the invention can be formulated for enteral, parenteral or topical administration. Indeed, all three types of formulations can be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

Quorum sensing regulators can also be incorporated into pharmaceutical compositions which allow for the sustained delivery of those compounds to a mammal for a period of several days, to at least several weeks, to a month or more. Such formulations are described in U.S. Pat. Nos. 5,968,895 and 6,180,608 B1.

For topical administration, any common topical formation such as a solution, suspension, gel, ointment or salve and the like can be employed. Preparation of such topical formulations are well described in the art of pharmaceutical formulations as exemplified, for example, by Remington's Pharmaceutical Sciences. For topical application, Quorum sensing regulators can also be administered as a powder or spray, particularly in aerosol form. The active ingredient can be administered in pharmaceutical compositions adapted for systemic administration. As is known, if a drug is to be administered systemically, it can be confected as a powder, pill, tablet or the like or as a syrup or elixir for oral administration. For intravenous, intraperitoneal or intra-lesional administration, the active ingredient will be prepared as a solution or suspension capable of being administered by injection. In certain cases, it may be useful to formulate the active ingredient in suppository form or as an extended release formulation for deposit under the skin or intramuscular injection. In a one embodiment, quorum sensing regulators can be administered by inhalation. For inhalation therapy the compound can be in a solution useful for administration by metered dose inhalers or in a form suitable for a dry powder inhaler.

It will be appreciated by those skilled in the art that various omissions, additions and modifications may be made to the invention described above without departing from the scope of the invention, and all such modifications and changes are intended to fall within the scope of the invention, as defined by the appended claims. All references, patents, patent applications or other documents cited are herein incorporated by reference in their entirety.

EXAMPLE 1

Experimental Procedures

A. Bacterial Strains and Media

*V. harveyi* strains are derived from BB120 (Bassler et al., 1997) and were grown at 30° C. with aeration in Luria-marine (LM), heart infusion (HI), or autoinducer bioassay (AB) broth (Bassler et al., 1994b; Freeman et al., 1999). *V. cholerae* strains are derivatives of El Tor strain C6706str2 (Thelin et al., 1996) and were grown at 30° C. with aeration in Luria-Bertani (LB) or SOC broth (Sambrook et al., 1989). For studies of toxin coregulated pilus (TCP), *V. cholerae* was grown at 37° C. in AKI medium under AKI conditions (Iwanaga et al., 1986). *E. coli* S17-1λpir (de Lorenzo et al., 1994) and JM109 (Yanisch-Perron et al., 1985) were used to propagate plasmids at 37° C. in LB. The following antibiotics were used: ampicillin (amp), 100 µg/ml; tetracycline (tet), 10 µg/ml; kanamycin (kan), 100 µg/ml; chloramphenicol (cm), 10 µg/ml; and gentamicin (gent), 100 µg/ml. Streptomycin (strep) was used at 1 mg/ml and polymyxcin B (pb) at 50 units/ml.

B. DNA Manipulations

All DNA manipulations were performed according to Sambrook et al. (1989). PFUTurbo® polymerase (Stratagene) was used for PCR reactions used in cloning, whereas Taq polymerase (Roche) was used for all other PCR reactions. dNTPs, restriction endonucleases, and T4 ligase were obtained from New England Biolabs. DNA purification kits were obtained from QIAGEN. *V. harveyi* deletions were constructed using the method of Datsenko and Wanner (2000). Constructions were placed on the *V. harveyi* chromosome by allele replacement (Bassler et al., 1993). In-frame deletions were constructed by the method of Skorupski et al., (1996). hapR-lacZ reporter fusions were constructed via the method of Kalogeraki et al., (1997). qrr1 from *V. cholerae* was overexpressed from plasmid pKK177-3RI (Brosius et al., 1984). For *V. harveyi*, a kan resistance cassette was also incorporated into pKK177-3RI. The qrr1-lux transcriptional fusion plasmid was constructed by ligating a PacI fragment from pCS26-Pac (Bjarnason et al., 2003) into an engineered PacI site in pBBR1MCS (Kovach et al., 1994). The vector was digested with BamHI, which eliminated a roughly 2 kb DNA fragment, and a PCR-amplified fragment containing the promoter region of *V. cholerae* qrr1 was cloned into the BamHI site.

C. Bioluminescence Assays

*V. harveyi* cultures were grown in AB broth for 14 hr at 30° C. with aeration. The cultures were diluted 1:5000 prior to bioluminescence assays, which were performed as described (Bassler et al., 1993). Relative light units for *V. harveyi* are defined as counts $min^{-1}$ $ml^{-1}$×$10^3$/cfu $ml^{-1}$. *V. cholerae* bioluminescence assays were performed following 10 hr growth at 30° C. in SOC containing tet to maintain the plasmid pBB1 carrying *V. harveyi* luxCDABE. $OD_{600\ nm}$ for each culture was measured, and the cultures were diluted such that each culture was at the same cell density (~1:1000 dilution). Light and $OD_{600\ nm}$ were measured every 45 min as described (Miller et al., 2002). Relative light units for *V. cholerae* are defined as counts $min^{-1}$ $ml^{-1}$/$OD_{600\ nm}$.

D. β-Galactosidase Assays

β-galactosidase assays were performed in triplicate as described by Slauch et al., (1991). β-galactosidase units are defined as [$V_{max}$][dilution factor]/$OD_{600\ nm}$.

E. Western Blot Analysis and Antibody Preparation

Western blot analysis was performed as described (Henke et al., 2004), the membranes were exposed to anti-TcpA antibody, and chemiluminescence detection (Amersham) was used (Sun et al., 1991). To analyze HapR and LuxR protein levels, HapR and LuxR were purified (Chen et al., 2002b), and polyclonal antibodies were generated (Henke et al., 2004). Polyclonal antisera were adsorbed to both *E. coli* pGEX-4T-1 lysates and either a *V. cholerae* hapR mutant lysate or a *V. harveyi* luxR mutant lysate prior to use.

F. Northern Blot Analysis

Cultures used for RNA preparations were grown to $OD_{600\ nm}$ of 0.5. Rifampicin was added at 100 µg/ml, and each culture was further incubated with aeration at 30° C. Aliquots were taken at the appropriate times, and RNA was extracted with TRIzol® reagent (Invitrogen) and chloroform. TRIzol reagent is a monophasic solution of phenol and guanidine isothiocyanate. RNA was precipitated with isopropanol, washed with 75% ethanol, and resuspended in DEPC water. Northern blots were performed as described (Martin et al., 1989). Steady-state Northern blots were performed as above except that no rifampicin was added.

G. Genetic Screen to Identify hfq

*V. harveyi* strain JAF548 (luxO D47E $kan^r$) was mutagenized with Mini-MulacZ ($cm^r$) as described (Martin et al., 1989). Bright colonies were isolated, and insertions in luxO and rpoN were identified by PCR and complementation. Tn5lacZ mutagenesis of hfq in cosmid pBNL2014 was carried out as described previously (Showalter et al., 1990). Transposon insertions were mapped by restriction analysis and sequencing. Cosmid pBNL2031, containing a Tn5lacZ insertion in hfq, was used in the allelic replacement procedure to generate BNL258 (hfq::Tn5lacZ).

EXAMPLE 2

A Genetic Screen for the *V. harveyi* Quorum-Sensing Repressor

A previously characterized LuxO allele, luxO D47E, was used to identify the repressor that acts downstream of LuxO (Freeman et al., 1999). The D47E mutation alters the site of phosphorylation, and "locks" the LuxO D47E protein into a state mimicking LuxO-P. The *V. harveyi* luxO D47E strain was mutagenized with the transposon Mini-MulacZ and screened for colonies that had acquired a bright phenotype, indicating that they had obtained a mutation bypassing the dark LuxO D47E phenotype.

Figure 2A:
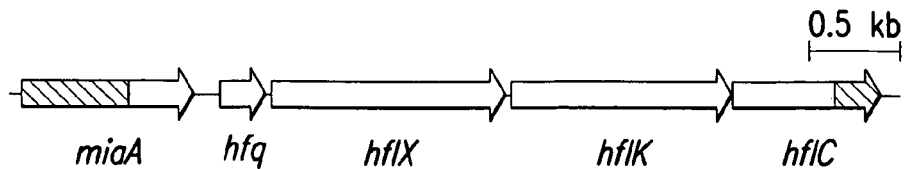
FIG. 2A graphically illustrates the hfq locus in *V. harveyi*. miaA and hflC were not fully sequenced (unsequenced regions are denoted by light-colored shading).

Of the 40,000 transposon insertion mutants generated, 85 were bright. The majority of these (82) contained transposon insertions in either luxO or rpoN, the gene encoding $\sigma^{54}$. Three bright mutants did not harbor mutations in either of these genes. A *V. harveyi* genomic cosmid library was introduced into one of these mutants (BNL211) and screened for restoration of the dark phenotype. All cosmids conferring a dark phenotype contained overlapping regions of DNA, suggesting that a single locus was responsible. One cosmid, pBNL2014, was mutated with Tn5lacZ to pinpoint the region responsible for lux repression. The region identified was cloned and sequenced and found to contain the gene hfq (FIG. 2A). The *V. harveyi* hfq gene displays high homology to hfq genes from other *Vibrio* species, including *V. parahaemolyticus*, *V. cholerae*, and *V. vulnificus*, with 100%, 95%, and 94% identity, respectively using the NCBI Blast program. The GenBank accession number for the *V. harvyei* hfq locus is AY578785. The *V. harveyi* hfq coding region sequences are provided as SEQ ID NO. 39 for the amino acid sequence and as SEQ ID NO.40 for the nucleotide sequence. The same sequence information is provided in SEQ ID NOS. 41 and 42, respectively, for the *V. cholerae* hfq coding region.

EXAMPLE 3

Hfq Regulates Quorum Sensing

Figure 2B:
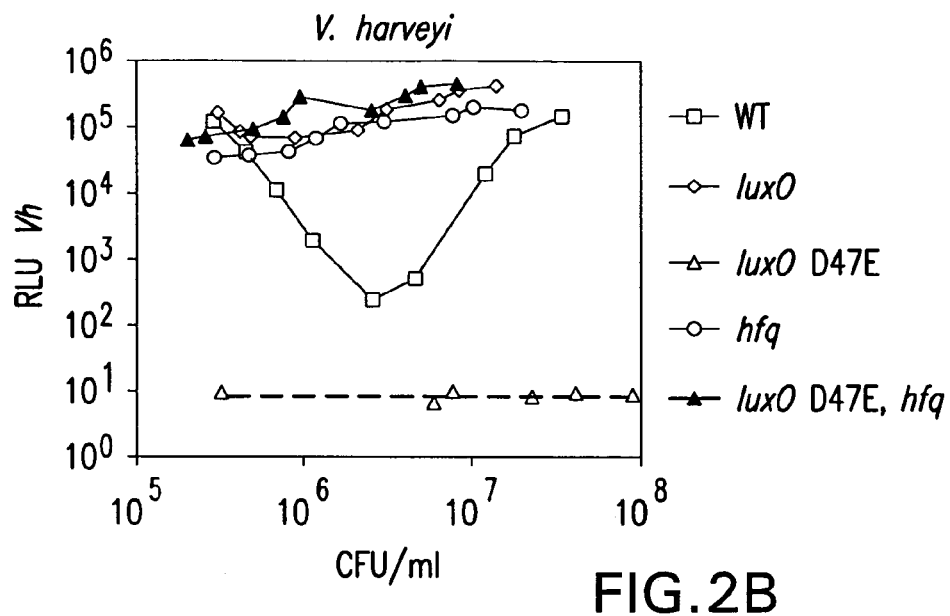
FIG. 2B shows a plot of bioluminescence versus cell density for *V. harveyi* strains BB120 (WT, squares), JAF78 (ΔluxO::cm$^r$, diamonds), JAF548 (luxO D47E, open triangles), BNL258 (hfq::Tn5lacZ, circles), and BNL211 (luxO D47E, hfq::Mini-MulacZ, closed triangles). Relative light units for *V. harveyi* are defined as counts min$^{-1}$ ml$^{-1}$×10$^3$/cfu ml$^{-1}$.

To verify that Hfq has a role in quorum-sensing regulation in *V. harveyi*, hfq null mutations were introduced onto the chromosomes of the *V. harveyi*, hfq wild-type and luxO D47E strains. The Lux phenotypes of the single hfq and double luxO D47E, hfq mutants were examined and compared to those of the wild-type, luxO, and luxO D47E *V. harveyi* strains (FIG. 2B). Wild-type *V. harveyi* displays typical quorum-sensing behavior (squares): it is very bright immediately following dilution into fresh medium, but, early in the assay, luminescence decreases precipitously (~1000-fold) due to dilution of the autoinducers to a level below that required for activation of lux. However, as the cells grow, endogenously produced autoinducers accumulate to the level required for detection. Light production commences and increases 1000-fold, ultimately reaching the predilution level. The luxO null strain (diamonds) is constitutively bright because, in the absence of LuxO, no lux repressor is produced. Conversely, the luxO D47E strain (open triangles) is dark. The hfq mutant (circles) has a phenotype indistinguishable from the luxO mutant, demonstrating that Hfq is required for repression of lux expression at low cell densities. The luxO D47E, hfq double mutant (closed triangles) is also constitutively bright, showing that repression of lux by Hfq occurs downstream of LuxO.

Figure 2C:
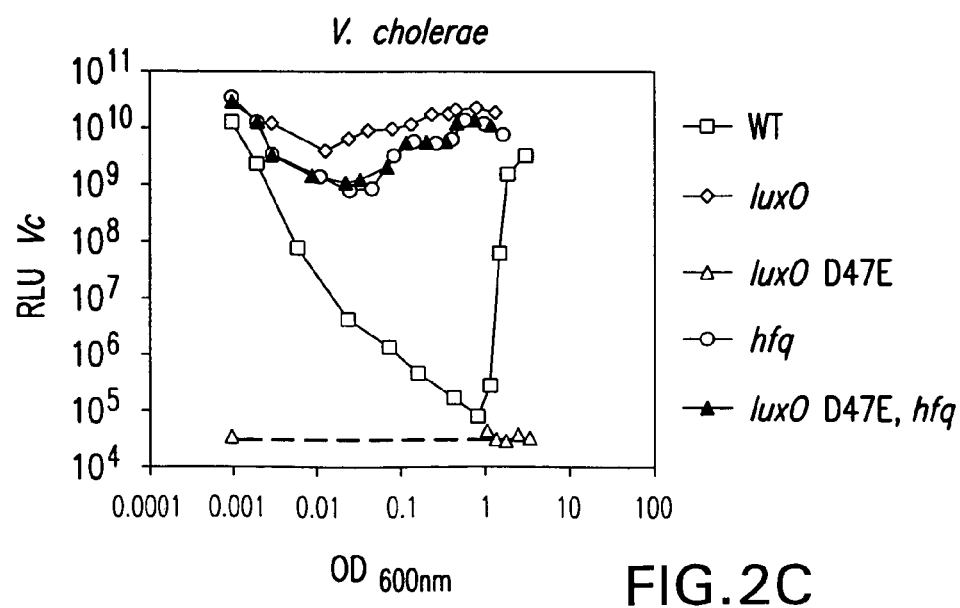
FIG. 2C shows bioluminescence versus cell density for *V. cholerae* strains MM227 (WT, squares), MM349 (ΔluxO, diamonds), BH48 (luxO D47E, open triangles), DL2078 (Δhfq, circles), and DL2378 (luxO D47E, Δhfq, closed triangles). Relative light units for *V. cholerae* are defined as counts min$^{-1}$ ml$^{-1}$/OD$_{600\ nm}$.

Hfq has the identical role in *V. cholerae* that it has in *V. harveyi* quorum sensing. Density-dependent light production from *V. cholerae* strains carrying *V. harveyi* lux was measured. The Lux phenotypes of the wild-type (squares), luxO (diamonds), luxO D47E (open triangles), hfq (circles), and luxO D47E, hfq (closed triangles) single and double *V. cholerae* mutants mimic the corresponding *V. harveyi* mutant phenotypes (FIG. 2C).

EXAMPLE 4

Hfq Regulates Virulence Gene Expression in *V. cholerae*

Figure 2D:
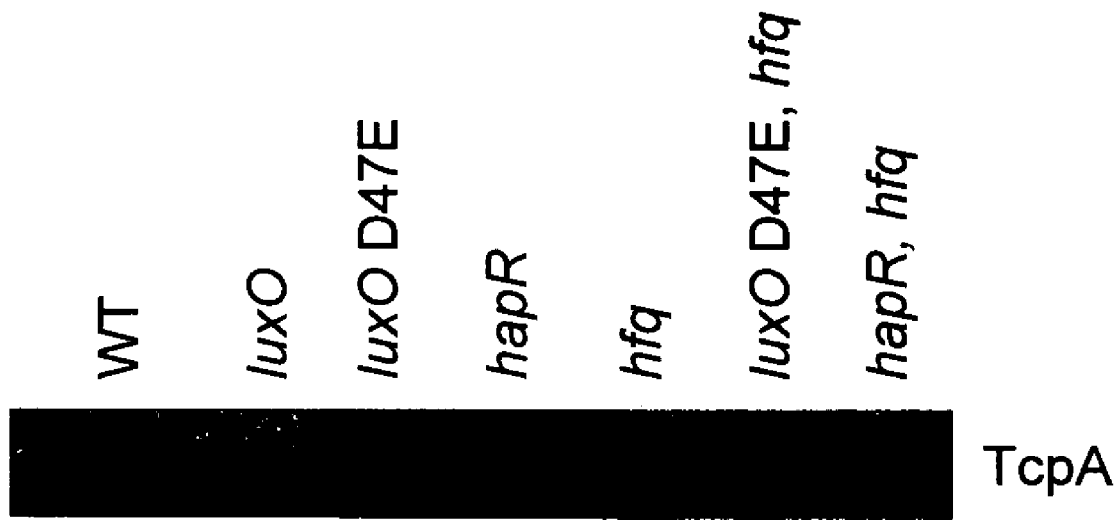
FIG. 2D is a Western blot showing the following *V. cholerae* strains analyzed for TcpA production: C6706str2 (WT), MM307 (ΔluxO), BH38 (luxO D47E), MM194 (ΔhapR), DL2066 (Δhfq), DL2146 (luxO D47E, Δhfq), and DL2607 (ΔhapR, Δhfq).

To show that the quorum-sensing activity of Hfq is not restricted to the normative lux target in *V. cholerae*, TcpA (the major subunit of the toxin-coregulated pilus) production was measured using Western blots (FIG. 2D) (Taylor, 1991). TcpA is present in the wild-type strain because, at low cell density, quorum sensing initiates the cascade leading to TcpA production, which enables its detection at high cell density (Zhu et al., 2002). No TcpA is observed in the luxO strain, because LuxO-P is required at low cell density to initiate the production of the TcpA observed in the wild-type. In contrast, high levels of TcpA are observed in the luxO D47E strain. Similarly, the hapR mutant that is also locked in low cell density mode produces high levels of TcpA. Low TcpA is detected in the hfq mutant, demonstrating that Hfq is required for virulence-factor expression. TcpA production in the double luxO D47E, hfq and hapR, hfq mutants demonstrates that Hfq acts downstream of LuxO and upstream of HapR in the quorum-sensing regulatory cascade.

EXAMPLE 5

Hfq Involvement in Quorum Sensing

In *E. coli* and other bacteria, Hfq binds a variety of small regulatory RNAs (sRNAs) and promotes interaction between the sRNAs and their target mRNAs (Masse et al., 2003b; Valentin-Hansen et al., 2004). These Hfq-sRNA complexes alter the stability/translation of the target mRNAs. The discovery that Hfq is required for quorum-sensing repression in *V. harveyi* and *V. cholerae* led to two predictions: first, quorum-sensing repression occurs posttranscriptionally, and, second, there must be one or more sRNAs involved. LuxO-P and $\sigma^{54}$ do not control transcription of hfq further suggested that, at low cell density, the LuxO-P $\sigma^{54}$ complex activates the transcription of the gene(s) encoding the sRNA(s).

A. Hfq Affects the Stability of luxR/hapR mRNA

LuxR and HapR appear to be the master regulators of their respective quorum-sensing regulons (Henke et al., 2004; Zhu et al., 2002).

Northern blots were used to determine the effect of hfq mutations on luxR and hapR mRNA stability in *V. harveyi* and *V. cholerae*. Rifampicin was added to cultures to terminate transcription, after which the luxR and hapR transcripts were monitored over time. The analysis was performed in luxO D47E strains to assess the fate of the luxR and hapR transcripts at low cell density. FIG. 3A shows that, under these conditions, both the luxR and hapR transcripts disappear immediately following termination of transcription (panels labeled luxO D47E). However, in the luxO D47E, hfq double mutants, the transcripts show significantly increased longevity (FIG. 3A, panels labeled luxO D47E, hfq). The control shows that mutation of hfq has no effect on the stability of rpsL mRNA (FIG. 3A, four lower panels). Western blots show that the increased stability of the luxR and hapR mRNAs in the hfq mutants leads to increased levels of the LuxR and HapR proteins (FIG. 3B). These results demonstrate that, at low cell density, Hfq destabilizes the luxR and hapR mRNA in *V. harveyi* and *V. cholerae*, respectively, which leads to reduced LuxR and HapR protein in the cells.

B. LuxO-P Regulation of hapR is Posttranscriptional and Requires Hfq

Figure 4A:
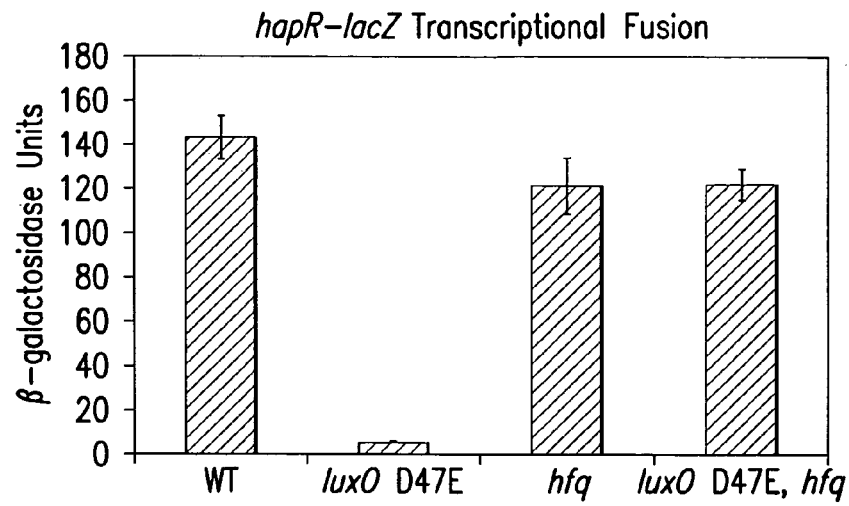
FIG. 4A shows β-galactosidase activity of hapR-lacZ transcription in *V. cholerae* DL2106 (WT, ΔlacZ), DL2099 (luxO D47E, ΔlacZ), DL2523 (Δhfq, ΔlacZ), and DL2441 (luxO D47E, Δhfq, ΔlacZ).
Figure 4B:
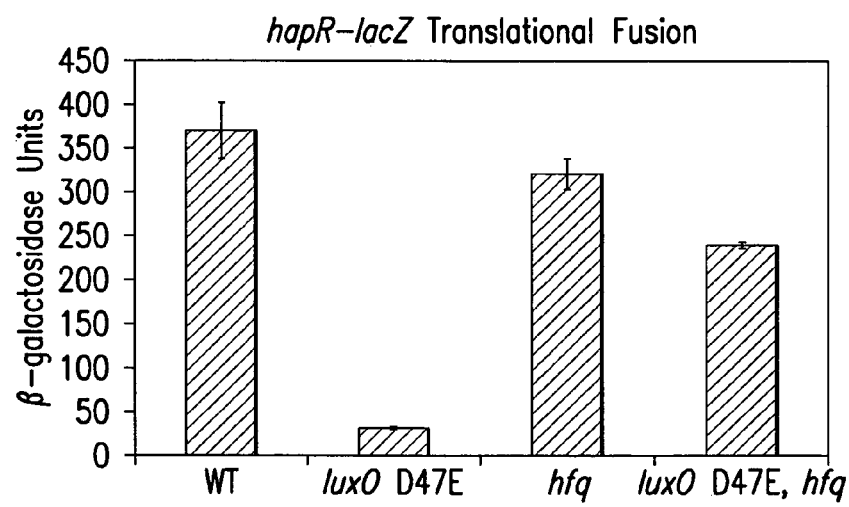
FIG. 4B shows β-galactosidase activity of hapR-lacZ translation in *V. cholerae* DL2543 (WT, ΔlacZ), DL2542 (luxO D47E, ΔlacZ), DL2531 (Δhfq, ΔlacZ), and DL2533 (luxO D47E, Δhfq, ΔlacZ).
Figure 4C:
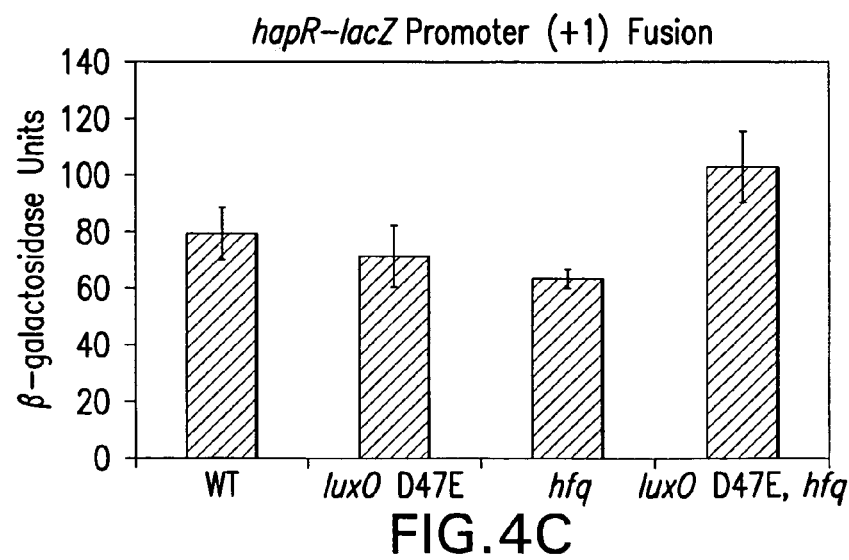
FIG. 4C shows β-galactosidase activity of hapR-lacZ promoter activity in *V. cholerae* DL2748 (WT, ΔlacZ), DL2771 (luxO D47E, ΔlacZ), DL2703 (Δhfq, ΔlacZ), and DL2698 (luxO D47E, Δhfq, ΔlacZ).

Previous analyses have suggested that LuxO-P controls transcription of hapR in *V. cholerae* (Zhu et al., 2002). To distinguish between transcriptional and posttranscriptional regulation of hapR, chromosomal hapR-lacZ transcriptional, translational, and promoter fusions were constructed and their activities were measured in the *V. cholerae* wild-type, luxO D47E, hfq, and luxO D47E, hfq strains. The transcriptional and translational fusions are repressed in the luxO D47E strain, and repression requires Hfq (FIGS. 4A and 4B, respectively). In contrast, LuxO D47E does not repress the hapR-lacZ promoter fusion in which lacZ fused to the predicted site of transcription initiation (+1 site) (FIG. 4C). These results suggest that LuxO-P of hapR is posttranscriptional and show that region between the predicted +1 site and the hapR coding region is required for Hfq control.

EXAMPLE 6

Identification of sRNAs Involved in Quorum-Sensing Using Bioinformatics

The findings point toward a LuxO-$\sigma^{54}$-regulated sRNA in the quorum-sensing signal-transduction circuits of *V. harveyi* and *V. cholerae*. These small genes are very difficult to identify by traditional genetic approaches, so a method to scan the *V. cholerae* genome for candidate sRNA loci was developed. For this analysis, the following parameters were used: (1) the upstream region of the locus must contain a $\sigma^{54}$ binding site; (2) since most sRNAs identified to date have Rho-independent terminators (Argaman et al., 2001; Chen et al., 2002a; Wassarman et al., 2001), the presence of a Rho-independent terminator was required; (3) since most sRNAs are located in intergenic regions (Argaman et al., 2001; Wassarman et al., 2001), the search was restricted to regions between annotated genes; and (4) the sRNA must be conserved in *V. cholerae, V. parahaemolyticus*, and *V. vulnificus*. The completed genome sequences of these vibrios show that they possess homologs of luxR/hapR, luxO, luxU, and hfq, suggesting that they have a conserved quorum-sensing regulatory mechanism (Chen et al., 2003; Heidelberg et al., 2000; Makino et al., 2003).

Using PATSER, the *V. cholerae* genome was scanned for potential $\sigma^{54}$ binding sites with a weight matrix constructed from a compiled set of ~180 $\sigma^{54}$ binding sites from multiple bacterial species (Barrios et al., 1999; Dombrecht et al., 2002; Hertz et al., 1999; van Helden, 2003). All hits above a cutoff score chosen to include all binding sites upstream of genes in *V. cholerae* that are known to be regulated by $\sigma^{54}$ were considered. In a parallel procedure, the upstream regions of the known *V. cholerae* $\sigma^{54}$-regulated genes were extracted, and searched with the program CONSENSUS for a 16 bp motif (Hertz et al., 1999). The motif so obtained corresponded perfectly to the known $\sigma^{54}$ binding sites in *V. cholerae*, with the consensus sequence 5'-TGGCAC-N$^5$-TTGCA/T-3' (SEQ ID NO. 43). The aligned set of binding sites was used to construct a weight matrix for $\sigma^{54}$ sites specific to *V. cholerae*. The weight matrices obtained by these two procedures were quite similar and the final result did not depend on the weight matrix used to scan the genome.

Figure 5A-1:
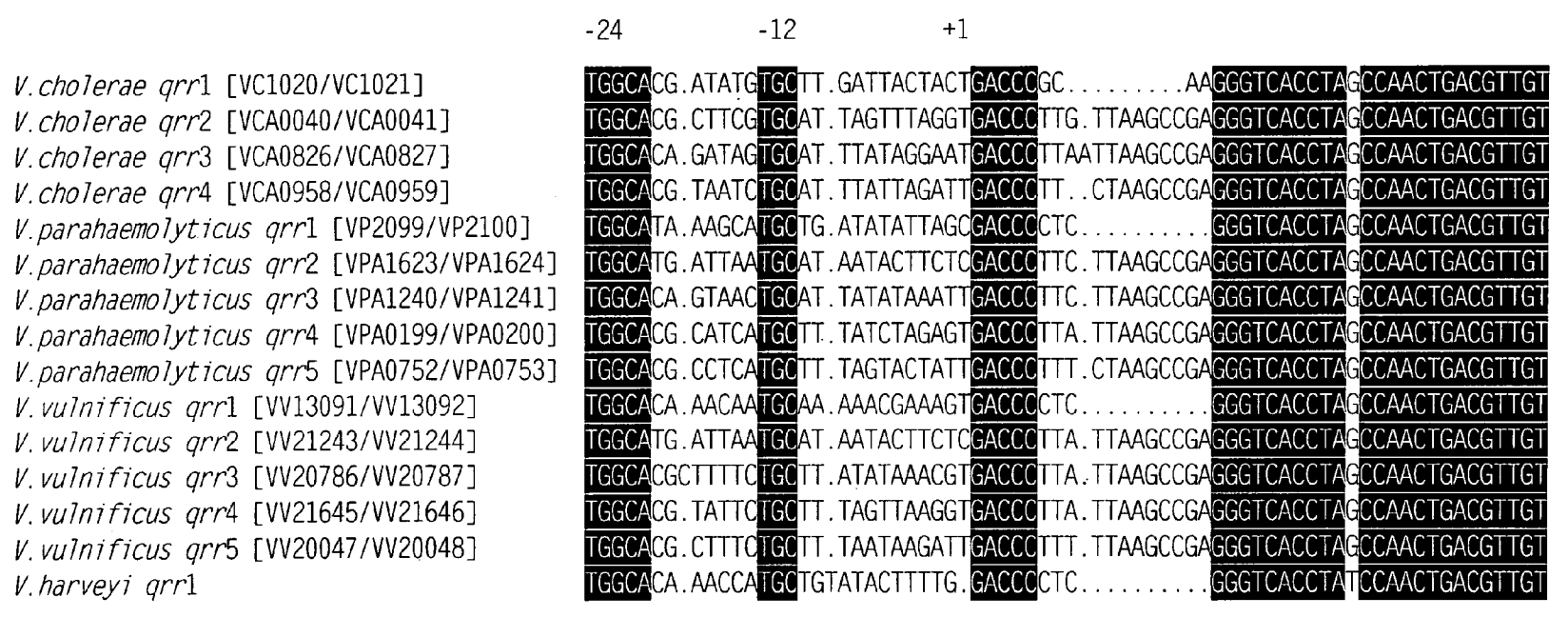
Figure 5A-2:
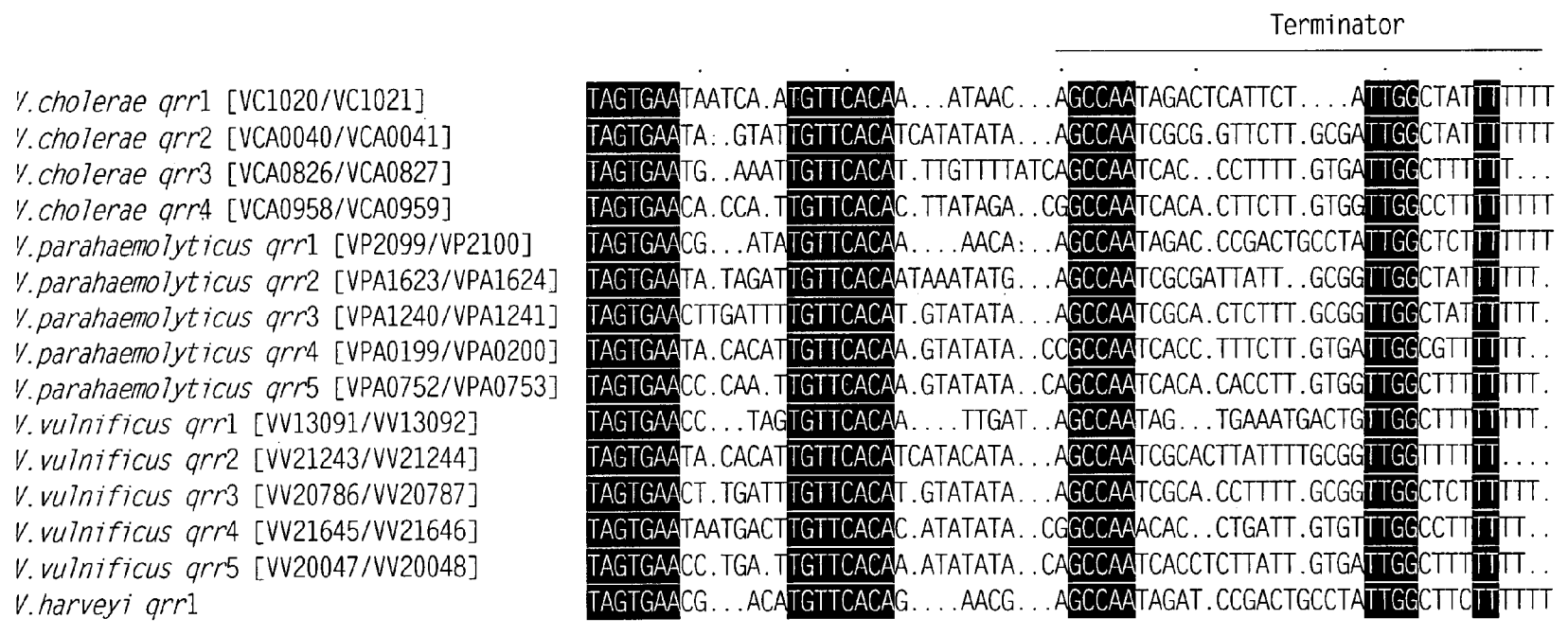

The analysis of *V. cholerae* identified several predicted $\sigma^{54}$ binding sites in intergenic regions. These regions were examined for conservation across the specified *vibrio* genomes and for the presence of Rho-independent terminators. These constraints narrowed the search to four intergenic regions. The sequences and alignment of these four regions are shown in FIG. 5A, along with the corresponding regions from *V. parahaemolyticus* and *V. vulnificus*. These four loci are highly homologous to one another. They all contain the signature $\sigma^{54}$ binding site and a terminator, suggesting that these elements are independently transcribed loci. These loci were designated as qrr1, qrr2, qrr3, and qrr4 (for quorum regulatory rna 1-4). Interestingly, one of the sRNA loci, qrr1, is located immediately upstream of luxO. In *V. parahaemolyticus* and *V. vulnificus*, a fifth putative sRNA locus was identified that fulfilled all of the search criteria (denoted qrr5).

Figure 5B:
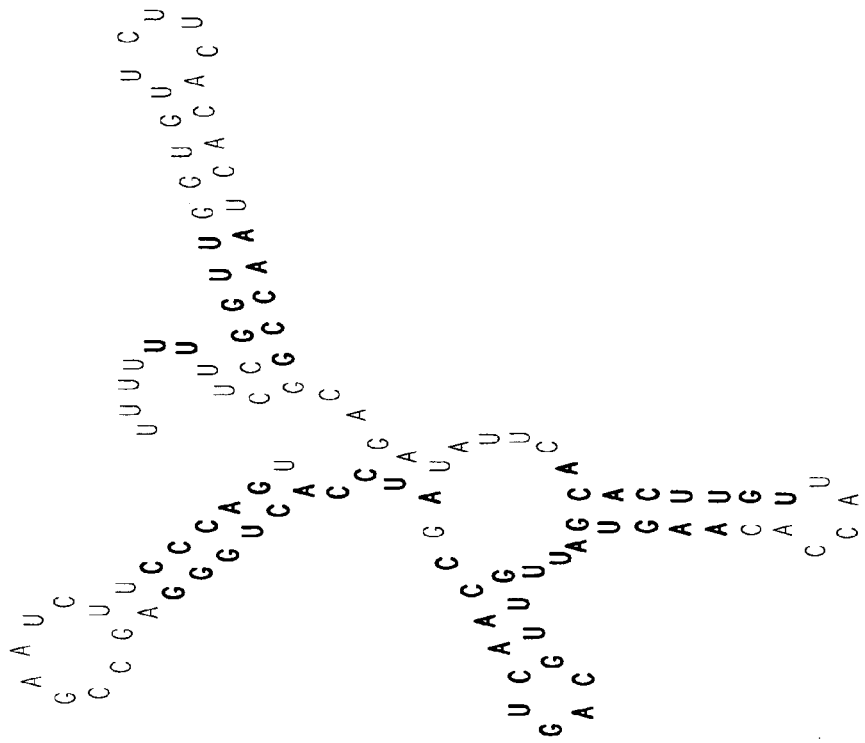
FIG. 5B illustrates the lowest-energy secondary-structural predictions for the Qrr sRNAs identified in *V. cholerae*. Bold typeface indicates the regions conserved across all sRNAs in *V. cholerae, V. parahaemolyticus*, and *V. vulnificus*.
Figure 2:
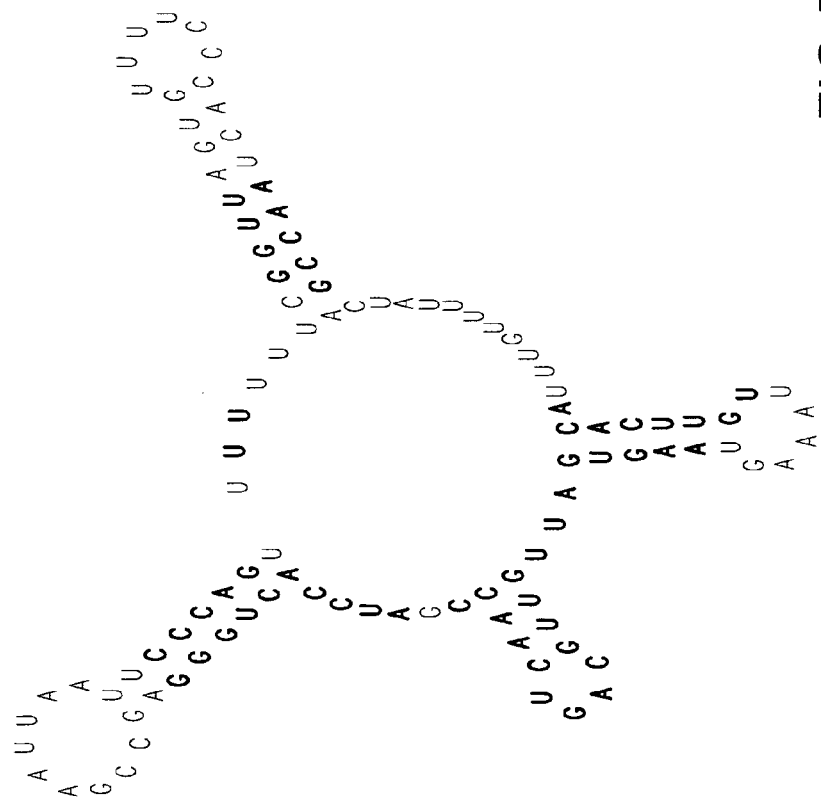

The RNAFOLD program was used to find the predicted secondary structures of the candidate sRNAs (FIG. 5B) (Hofacker, 2003). The predicted structures of Qrr2 and Qrr3 are very similar, as is the structure of Qrr4 if the three nucleotide pairs joining the two center loops are melted (and note these three nucleotide pairs are not conserved across species). Thus, only the predicted structure of Qrr1 is obviously distinct. Qrr2 and Qrr3 show a site similar to the proposed Hfq binding site, which is an 8-12 nucleotide AU-rich region adjacent to stem loops (Moll et al., 2003). The composition of the loops is variable across species, but the stems are highly conserved, supporting the folding predictions. Many small regulatory RNAs act by base pairing to complementary regions in the 5' untranslated region of the mRNA. Using the program LALIGN, which finds the best local alignment of the input sequences, the complement of the hapR untranslated upstream region was aligned with all four *V. cholerae* sRNAs and the luxR upstream region with *V. harveyi* Qrr1 (FIGS. 5C and 5D, respectively). Interestingly, the region identified as being potentially involved in the complementary base pairing is absolutely conserved among all four sRNA candidates, with a single base difference in *V. harveyi* qrr1 (FIG. 5A). The highly conserved region overlaps the hapR and luxR putative ribosome binding sites (AAGGAUAU for hapR and AAG-GAAAA for luxR). Finally, analysis of the upstream regions of hapR and luxR and their orthologs across all the sequenced vibrios indicates that this region of interaction with the sRNAs is strongly conserved.

EXAMPLE 7

LuxO-P-$\sigma^{54}$ Controls the Expression of the sRNA Loci

It appears that the four putative sRNA loci in *V. cholerae*, and possibly five in *V. parahaemolyticus, V. vulnificus*, and *V. harveyi*, are regulated by LuxO-P together with $\sigma^{54}$. Analysis of the up-stream regions of the candidate sRNA loci shows a highly conserved region upstream of the $\sigma^{54}$ site. This site has dyad symmetry, and the consensus sequence is TTGCAW$_3$TGCAA (where W corresponds to A/T; SEQ ID NO. 46).

Figures 6A, 6B:
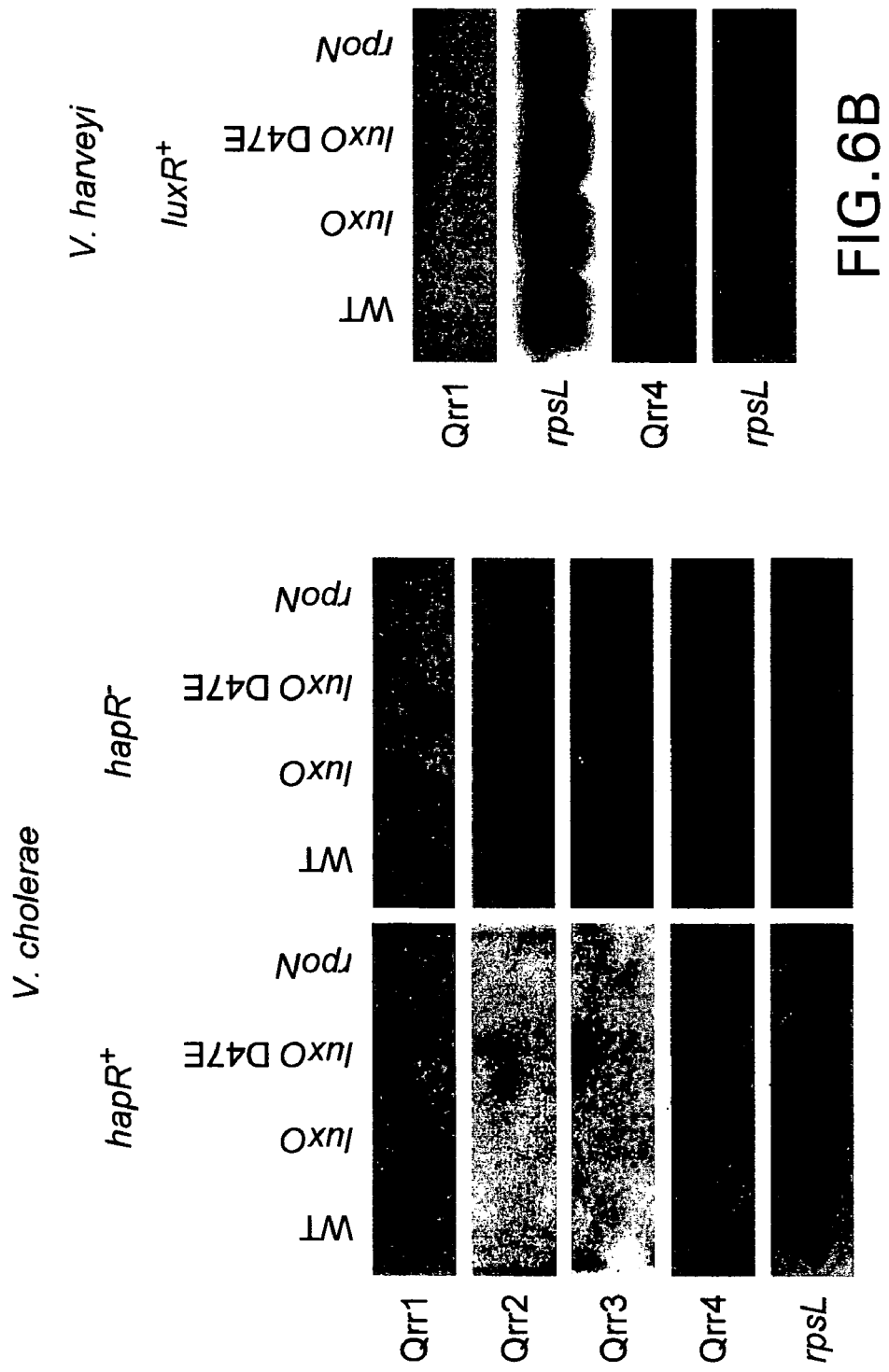
FIG. 6 illustrates the regulation of expression of the sRNAs by quorum sensing. For FIG. 6A, RNA isolated from *V. cholerae* C6706str2 (WT), MM307 (ΔluxO), BH38 (luxO D47E), BH76 (ΔrpoN) was probed for sRNAs Qrr1, Qrr2, Qrr3, and Qrr4, and *V. cholerae* rpsL (as a loading control). In the right panel of FIG. 6A, the hapR gene was deleted from the same set of strains and probed as described. For FIG. 6B, RNA isolated from *V. harveyi* BB120 (WT), BB721 (luxO::Tn5lacZ), JAF548 (luxO D47E), and BNL240 (rpoN::cm$^r$) was probed for sRNA Qrr1 with a probe made against *V. harveyi* qrr1 and for sRNA Qrr4 with a probe made against *V. cholerae* qrr4. *V. harveyi* rpsL is shown as the loading control.
FIG. 6C is a bar graph illustrating bioluminescence (RLU) at single time point for *V. cholerae* strains DL3212 (luxO) and DL3213 (luxO D47E) containing the qrr1-lux transcriptional fusion in trans.

To ascertain whether any of the candidate sRNA loci is a target of LuxO-P-$\sigma^{54}$ regulation in *V. cholerae*, Northern blot analysis was used to quantify transcript levels. The DNA encoding the putative sRNAs was amplified by PCR and used to probe identical Northern blots containing RNA isolated from low cell density cultures of wild-type, luxO, luxO D47E, and rpoN *V. cholerae* strains. FIG. 6A (hapR$^+$ panel) shows that, surprisingly, only Qrr4 is obviously regulated by LuxO-P-$\sigma^{54}$. A very small amount of this sRNA is detected in wild-type cells, whereas high levels are present in the luxO D47E strain. Importantly, Qrr4 is undetectable in both the luxO and rpoN mutants, consistent with a requirement for both LuxO-P and $\sigma^{54}$ for activating the expression of the locus encoding Qrr4 at low cell density. The other three *V. cholerae* sRNAs were not detected in this analysis.

Recently, it was shown in *E. coli* that, upon binding its mRNA target, the sRNA RyhB is degraded along with the target by RNaseE (Masse et al., 2003a). In the absence of the mRNA targets, increased stability of RyhB is observed. Accordingly, it was possible that the Qrr sRNAs were being degraded along with the hapR target mRNA. To test this, hapR was deleted in the wild-type, luxO, luxO D47E, and rpoN *V. cholerae* strains and RNA was prepared. Northern blots were run and probed for all four sRNAs (FIG. 6A, hapR$^-$ panel). In the absence of hapR mRNA, an increase in the level of Qrr4 is observed in the wild-type and luxO D47E strains. Minor amounts of Qrr2 and Qrr3 are also detected in the luxO D47E strain, showing that they are indeed regulated by LuxO-P and that their levels increase in the absence of hapR mRNA. However, the sRNA Qrr1 was not detected.

Additionally, qrr1 resides up-stream of luxO in *V. harveyi* but was not detected by Northern blot (FIG. 6B). However, Qrr4 from *V. harveyi* was detected by probing total RNA with the DNA probe made from the *V. cholerae* qrr4 PCR product, showing that such an sRNA exists in *V. harveyi*, and its expression is induced by LuxO D47E (FIG. 6B).

Figure 6C:
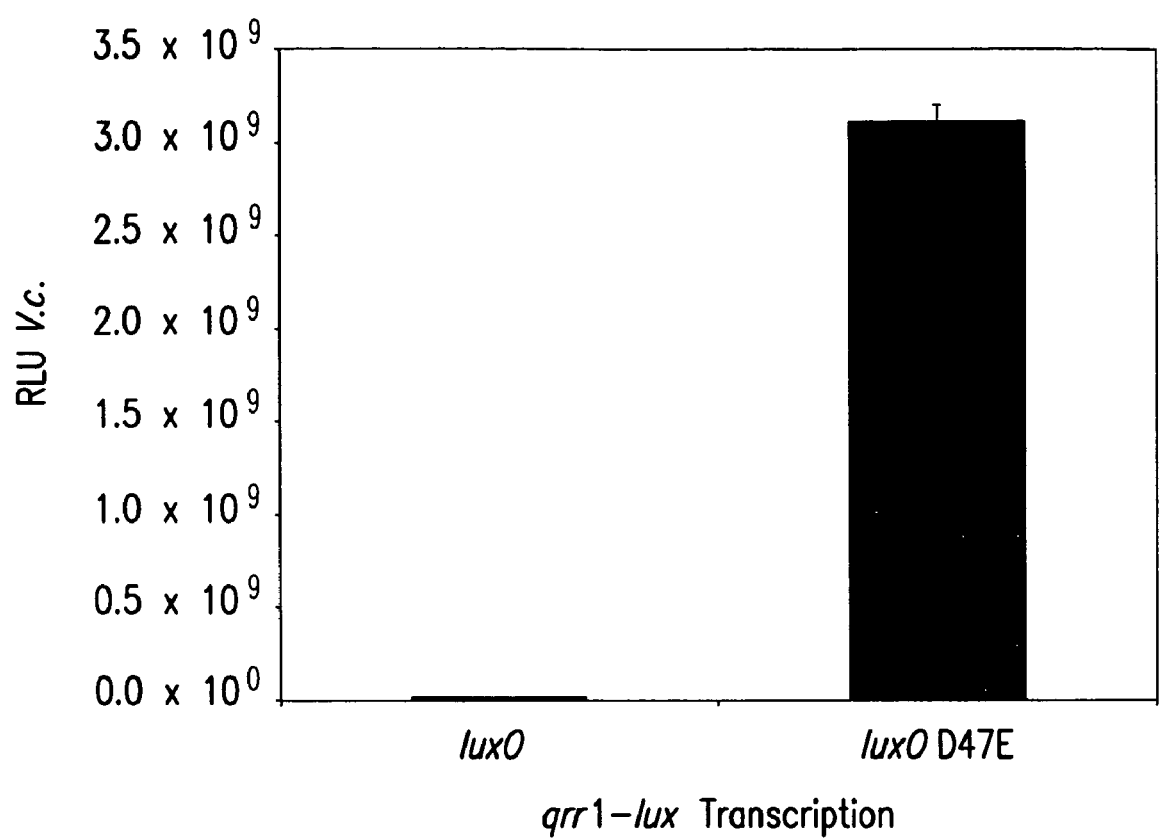

The inability to detect *V. cholerae* and *V. harveyi* Qrr1 could be a consequence of extremely low expression of qrr1 or instability of the qrr1 transcript, coupled with the insensitivity of the Northern blot procedure. Alternatively, expression of qrr1 might not be controlled by LuxO-P; however, this seemed unlikely, based on the bioinformatics analysis. To eliminate this latter possibility, a qrr1 transcriptional reporter was constructed by fusing the upstream region of *V. cholerae* qrr1 to the luxCDABE (luciferase) operon and tested for the expression of the qrr1-lux fusion in the luxO null and luxO D47E *V. cholerae* strains. The presence of LuxO D47E causes a 220-fold increase in expression from the qrr1 promoter, verifying that, indeed, qrr1 is regulated by LuxO-P (FIG. 6C). It also seemed possible that the absence of the Qrr2-4 sRNAs might lead to enhanced expression of the remaining qrr gene, qrr1. However, no change in transcription of qrr1-lux occurred in the triple mutant, suggesting that the presence or absence of qrr2-4 does not affect the expression of qrr1. Nevertheless, it appears that transcription of all four qrr genes is regulated by LuxO-P.

EXAMPLE 8

Four sRNAs are Involved in Quorum-Sensing Repression in *V. cholerae*

Figure 7A:
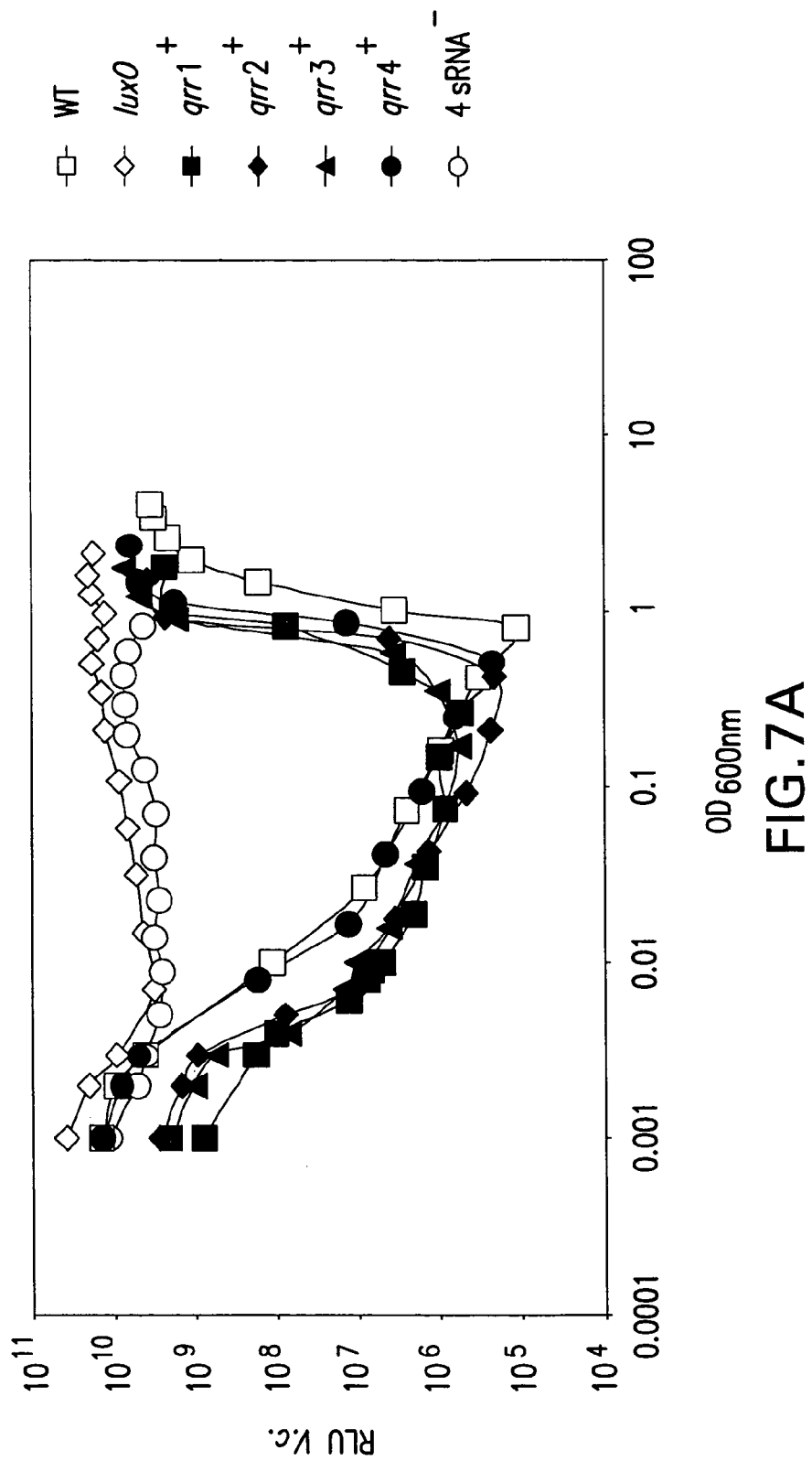
FIG. 7A graphically illustrates that simultaneous deletion of the four sRNAs is required to affect quorum sensing in *V. cholerae*.

To gain insight into the individual roles of the four sRNAs in quorum sensing, single, double, triple, and the quadruple qrr sRNA deletions were constructed in *V. cholerae* and density-dependent light production was measured. Only the simultaneous deletion of all four sRNAs affected bioluminescence expression (FIG. 7A). The results are shown for each triple mutant and the quadruple mutant. Single and double sRNA deletion mutants behaved similarly to the triple mutants. The results show that if any one of the four sRNAs is present, *V. cholerae* expresses density-dependent bioluminescence similar to the wild-type. However, deletion of all four sRNA genes together results in a constitutive lux phenotype identical to the luxO null mutant. Thus, all four sRNAs participate in quorum-sensing repression, although any one alone is sufficient.

Because deletion of the sRNAs eliminates quorum-sensing repression in *V. cholerae*, it follows that overexpression of the sRNAs should result in constitutive repression. This possibility was tested by overexpressing *V. cholerae* qrr1 in various *V. cholerae* and *V. harveyi* strains and examining the impact on light production. Compared to the vector-alone control, when *V. cholerae* qrr1 is overexpressed in *V. cholerae*, light production is reduced to 21% in the wild-type, 10% in the luxO null strain, and 1% in the quadruple sRNA mutant. Overexpression of *V. cholerae* qrr1 in *V. harveyi* reduces light production to 12% in the wild-type and to 3% in the luxO null strain. Thus, the *V. cholerae* sRNA Qrr1 functions in both *V. cholerae* and *V. harveyi* to repress quorum sensing.

Figure 7B:
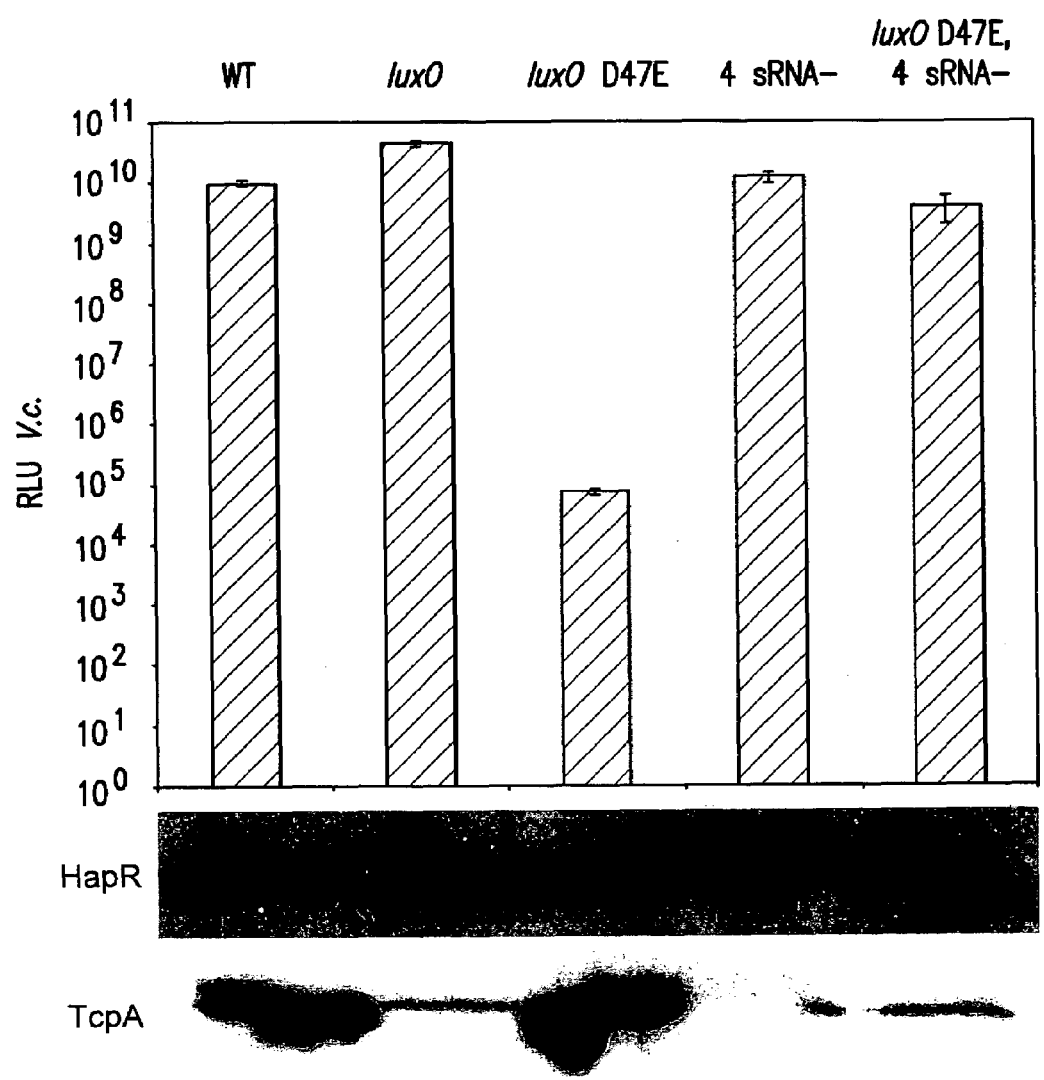
FIG. 7B is a bar graph (top panel) illustrating bioluminescence (RLU) at a single time point for *V. cholerae* strains MM227 (WT), MM349 (ΔluxO), BH48 (luxO D47E), DL2956 (Δqrr1, Δqrr2, Δqrr3, Δqrr4), and DL3024 (luxO D47E, Δqrr1, Δqrr2, Δqrr3, Δqrr4). The bottom two panels are Western blots probed for HapR and TcpA production from *V. cholerae* strains C6706str2 (WT), MM307 (ΔluxO), BH38 (luxO D47E), DL2953 (Δqrr1, Δqrr2, Δqrr3, Δqrr4), and DL3020 (luxO D47E, Δqrr1, Δqrr2, Δqrr3, Δqrr4).

The data presented herein suggests that multiple sRNAs act downstream of LuxO-P to destabilize luxR/hapR mRNA and regulate quorum-sensing dependent gene expression in *V. harveyi* and *V. cholerae*. To verify this model, an epistasis test was performed in *V. cholerae*. For this test, light production and HapR and TcpA protein levels were measured in the *V. cholerae* wild-type strain, the luxO null mutant, the luxO D47E mutant, the quadruple sRNA deletion mutant, and the luxO D47E mutant containing the quadruple deletion of the qrr genes (FIG. 7B). Maximal light is produced and a corresponding high level of HapR protein is observed in the high cell density wild-type and luxO strains. Both light and HapR protein levels are severely reduced in the luxO D47E strain. However, deletion of the four sRNAs alone or in the luxO D47E background restores maximal light production and maximal HapR protein production, showing that the four sRNAs are required for repression and act downstream of LuxO. Because lux and tcpA are regulated in an opposite manner by quorum sensing, TcpA levels are expected to vary reciprocally with those of lux expression and HapR concentration in the quorum-sensing mutants. FIG. 7B shows this is the case and that the four sRNAs are epistatic to LuxO-P in regulation of tcpA.

EXAMPLE 9

Regulatory Kinetics Model

Figure 8:
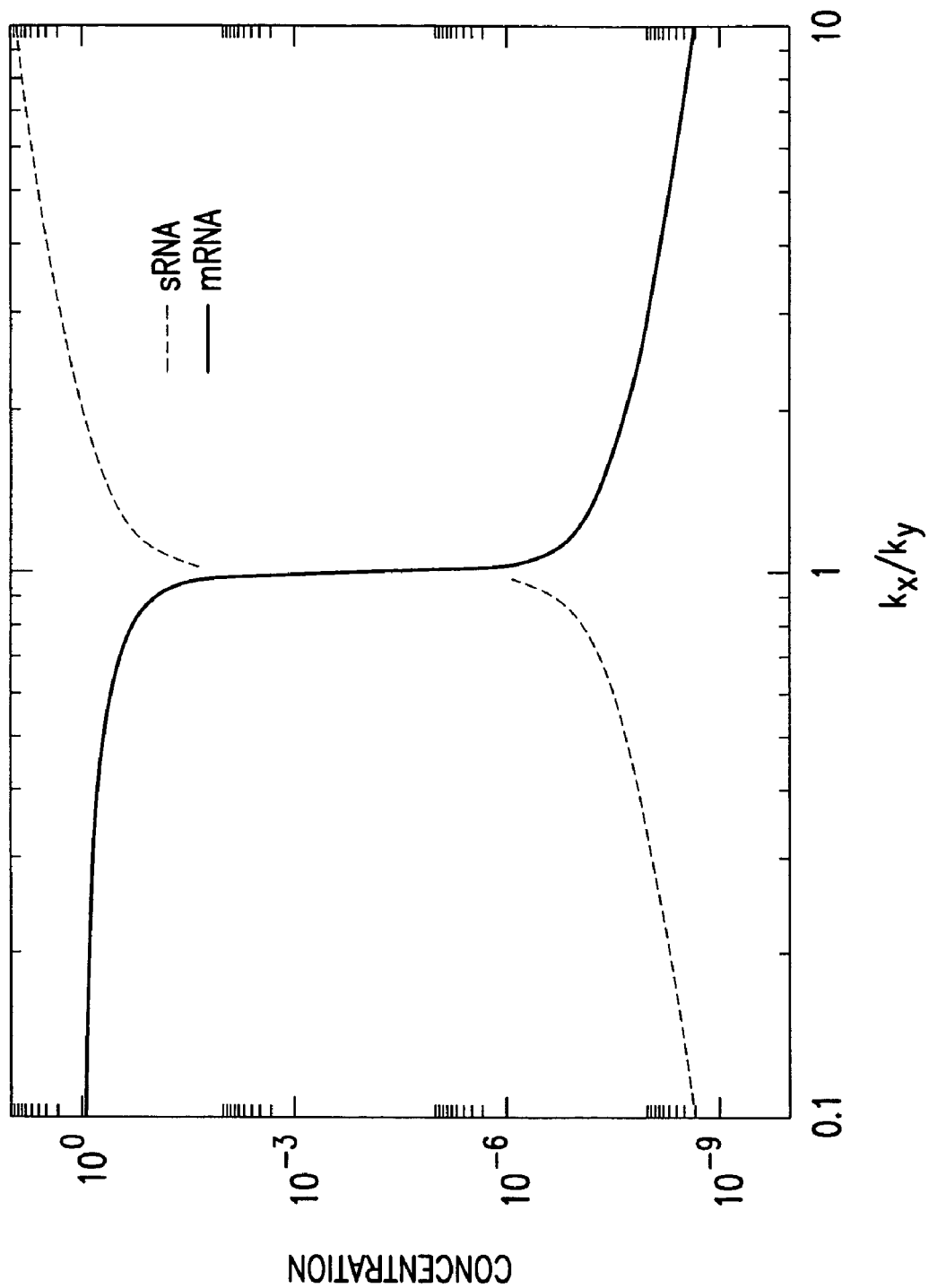
FIG. 8 graphically depicts a rate model showing that mutual destruction of sRNA and its target mRNA produces an ultrasensitive response to the rate of sRNA synthesis. If the rate of sRNA synthesis, $k_x$, drops below the rate of target mRNA synthesis, $k_y$, the steady-state pool of target message rises abruptly. In the quorum-sensing circuit, this implies that an ultrasensitive increase in hapR/luxR mRNA levels occurs with decreasing levels of LuxO-P as cell density increases. The curves are generated from Equation 7 of Elf et al. (2003), which describes the production of two chemical species (the sRNA and the mRNA) that undergo mutual destruction with a second-order rate constant $k_{md}(=v_{max}/K_x K_y)$ and also undergo intrinsic, first-order degradation at a rate μ. In the curves shown, the one adjustable parameter $k_{md}k_y/\mu^2$ equals $5\times10^7$, which is in the regime where degradation of the minority species is primarily due to mutual-destruction processes. Concentrations are given in units of $k_y/\mu$.

Why does LuxO regulate hapR/luxR via sRNAs rather than directly? One reason may be that the sRNAs allow a simple "inversion" of regulatory control, so that the activator LuxO can repress hapR/luxR. However, this inversion could also be accomplished in other ways, e.g., by switching the regulation pattern of hapR/luxR with respect to its target genes. A more fundamental motivation for control via sRNAs may be to achieve an ultrasensitive (switchlike) response to the level of LuxO-P. As base pairing of an sRNA with its target message is known to promote degradation of both the sRNA and the message, this "mutual destruction" provides an elegant mechanism for ultrasensitivity. Specifically, as shown in FIG. 8, if the rate of synthesis of a particular sRNA exceeds the rate of synthesis of its target message, even if only slightly, then the sRNA can accumulate in the cell, and target message levels can be reduced to very low levels. In contrast, if the rate of synthesis of a particular target message exceeds that of its regulatory sRNA, then the message can accumulate (FIG. 8). The ultrasensitive mechanism described here also applies in the case of multiple sRNAs interacting with one or more mRNA targets (Paulsson et al., 2001).

The use of sRNAs to accomplish an ultrasensitive response may be particularly apt for processes such as quorum sensing in which an all-or-nothing response is indicated. Similarly, this all-or-nothing requirement could explain why sRNAs control the entry into stationary phase. A different kind of sRNA switch was highlighted by Masse et al. (2003a) for the RyhB system. In this case, the sRNA RyhB was shown to mediate a rapid, reversible switch in time in response to a large change in input (e.g., addition of iron to the medium). In the quorum-sensing circuit, by contrast, the switch occurs in response to a small change in input (e.g., LuxO-P levels) that is strongly amplified into a transition between two discrete states (e.g., low and high cell density). How fast this switch occurs in time will depend on the rate of change of LuxO-P levels as well as on the rate of accumulation and/or degradation of luxR/hapR mRNA and LuxR/HapR protein. Interestingly, an ultrasensitive response to LuxO-P via the rate of sRNA production puts a premium on precisely controlling the transcription rate of the sRNAs, consistent with the hypothesis that the presence of multiple sRNAs represents a mechanism for fine tuning the transition between low and high cell density states.

REFERENCES

Argaman et al. (2001) Curr. Biol. 11, 941-950.
Barrios et al. (1999) Nucleic Acids Res. 27, 4305-4313.
Bassler et al. (1993) Mol. Microbiol. 9, 773-786.
Bassler et al. (1994a) Mol. Microbiol. 13, 273-286.
Bassler et al. (1994b) Mol. Microbiol. 12, 403-412.
Bassler et al. (1997) J. Bacteriol. 179, 4043-4045.
Benson et al. (1994) Proc. Natl. Acad. Sci. USA 91, 4989-4993.
Bjarnason et al. (2003) J. Bacteriol. 185, 4973-4982.
Brosius et al. (1984) Proc. Natl. Acad. Sci. USA 81:6929-6933.
Cao et al. (1989) J. Biol. Chem. 264, 21670-21676.
Chen et al. (2002a) Biosystems 65, 157-177.
Chen et al. (2002b) Nature 415, 545-549.
Chen et al. (2003) Genome Res. 13, 2577-2587.
Datsenko et al. (2000) Proc. Natl. Acad. Sci. USA 97, 6640-6645.
de Lorenzo et al. (1994) Methods Enzymol. 235, 386-405.
Dombrecht et al. (2002) Genome Biol 3. Published online Nov. 26, 2002. RESEARCH0076.1-0076.11.
Elf et al. (2003) Biophys. J. 84, 154-170.
Federle et al. (2003) J. Clin. Invest. 112, 1291-1299.
Freeman et al. (1999) Mol. Microbiol. 31, 665-677.
Freeman et al. (2000a) J. Bacteriol. 181, 899-906.
Freeman et al. (2000b) Mol. Microbiol. 35, 139-149.
Fuqua et al. (2001) Annu. Rev. Genet. 35, 439-468.
Gennaro et al., (1995) Remington's Pharmaceutical Sciences, Mack Publishing Company.
Gouet et al. (1999) Bioinformatics 15, 305-308.
Hammer et al. (2003) Mol. Microbiol. 50, 101-104.
Heidelberg et al. (2000) Nature 406, 477-483.
Henke et al. (2004) J. Bacteriol., in press. [do you have this site?]
Hertz et al. (1999) Bioinformatics 15, 563-577.
Hofacker (2003) Nucleic Acids Res. 31, 3429-3431.
Iwanaga (1986) Microbiol. Immunol. 30, 1075-1083.
Jobling et al. (1997) Mol. Microbiol. 26, 1023-1034.
Kalogeraki et al. (1997) Gene 188, 69-75.
Kovach et al. (1994) Biotechniques 16, 800-802.
Kovacikova et al. (2002) Mol. Microbiol. 46, 1135-1147.
Lilley et al. (2000) Mol. Microbiol. 36, 940-954.
Makino et al. (2003) Lancet 361, 743-749.
Martin et al. (1989) J. Bacteriol. 171, 2406-2414.
Masse et al. (2003a) Genes Dev. 17, 2374-2383.
Masse et al. (2003b) Curr. Opin. Microbiol. 6, 120-124.
Miller et al. (2001) Annu. Rev. Microbiol. 55, 165-199.
Miller et al. (2002) Cell 110, 303-314.
Miyamoto et al. (1994) Mol. Microbiol. 14, 255-262.
Mok et al. (2003) EMBO J. 22, 870-881.
Moll et al. (2003) RNA 9, 1308-1314.
North et al. (1996) J. Mol. Biol. 260, 317-331.
Paulsson et al. (2001) Q. Rev. Biophys. 34, 1-59.
Reitze et al. (1985) Proc. Natl. Acad. Sci. USA 82, 1979-1983.
Sambrook et al. (1989) Molecular Cloning: A Laboratory Manual (Cold Spring Harbor, N.Y.: Cold Spring Harbor Laboratory Press).
Showalter et al. (1990) J. Bacteriol. 172, 2946-2954.
Skorupski et al. (1996) Gene 169, 47-52.
Slauch et al. (1991) J. Bacteriol. 173, 4039-4048.
Sun, et al. (1991) Infect. Immun. 59, 114-118.
Surette et al. (1999) Proc. Natl. Acad. Sci. USA 96, 1639-1644.
Taylor (1991) J. Chemother. Suppl. 13, 190-195.
Thelin et al. (1996) Infect. Immun. 64, 2853-2856.
Thompson et al. (1994) Nucleic Acids Res. 22, 4673-4680.
Valentin-Hansen et al. (2004) Mol. Microbiol. 51, 1525-1533.
Vance et al. (2003) Infect. Immun. 71, 2571-2576.
van Helden (2003). Nucleic Acids Res. 31, 3593-3596.
Wassarman et al. (2001) Genes Dev. 15, 1637-1651.
Wingrove et al. (1994) Genes Dev. 8, 1839-1852.
Wu et al. (1997) Mol. Microbiol. 24, 233-239.
Xavier et al. (2003) Curr. Opin. Microbiol. 6, 191-197.
Yanisch-Perron et al. (1985) Gene 33, 103-119.
Zhu et al. (2003) Dev. Cell 5, 647-656.
Zhu et al. (2002) Proc. Natl. Acad. Sci. USA 99, 3129-3134.

---

We claim:

1. A method of identifying a quorum-sensing regulator which comprises:
   (a) contacting *Vibrio* cells comprising at least one inactivated qrr gene with a test compound, wherein a qrr gene is a gene that encodes a small regulatory RNA (sRNA);
   (b) assaying a quorum sensing response to said compound; and
   (c) determining whether said test compound is a quorum-sensing regulator.

2. The method of claim 1, wherein said *Vibrio* cells comprise no more than one active qrr gene.

3. The method of claim 2, wherein assaying a quorum sensing response is measuring cell density-dependent changes of a reporter system.

4. The method of claim 3, wherein said reporter system comprises the *V. harveyi* lux operon, a lux promoter operably linked to a reporter molecule or a quorum-sensing promoter operably linked to a reporter molecule.

5. The method of claim 3, wherein said reporter molecule is β-galactosidase, a green fluorescent protein or a fluorescent variant derivative thereof, a luciferase, chloramphenicol acetyl transferase, β-glucuronidase, alkaline phosphatase and horseradish peroxidase.

6. The method of claim 2, wherein said *Vibrio* is *V. cholerae* comprising a lux operon or is *V. harveyi*.

7. The method of claim 2, wherein said *Vibrio* cells comprise one active qrr gene and said method identifies activators of quorum sensing.

8. The method of claim 2, wherein said *Vibrio* cells comprise no active qrr gene and said method identifies inactivators of quorum sensing.

9. The method of claim 1 wherein said qrr gene is selected from the qrr genes of *V. cholerae*, *V. harveyi*, *V. parahaemolyticus*, and *V. vulnificus*.

* * * * *

UNITED STATES PATENT AND TRADEMARK OFFICE
CERTIFICATE OF CORRECTION

| | | |
|---|---|---|
| PATENT NO. | : 7,405,050 B2 | Page 1 of 1 |
| APPLICATION NO. | : 11/104705 | |
| DATED | : July 29, 2008 | |
| INVENTOR(S) | : Lenz et al. | |

It is certified that error appears in the above-identified patent and that said Letters Patent is hereby corrected as shown below:

At col. 1, line 12, before "Therefore," please insert the following sentence:
--The grants are NSF Grant # MCB-0343821, NIH Grant 5ROI GM65859, and ONR Grant # N00014-03-0183.--

Signed and Sealed this

Fourteenth Day of October, 2008

JON W. DUDAS
*Director of the United States Patent and Trademark Office*

SEQUENCE LISTING

```
<160> NUMBER OF SEQ ID NOS: 46

<210> SEQ ID NO 1
<211> LENGTH: 96
<212> TYPE: DNA
<213> ORGANISM: Vibrio cholerae

<400> SEQUENCE: 1
tgacccgcaa gggtcaccta gccaactgac gttgttagtg aataatcaat gttcacaaat      60
aacagccaat agactcattc tattggctat tttttt                                96

<210> SEQ ID NO 2
<211> LENGTH: 108
<212> TYPE: DNA
<213> ORGANISM: Vibrio cholerae

<400> SEQUENCE: 2
tgacccttgt taagccgagg gtcacctagc caactgacgt tgttagtgaa tagtattgtt      60
cacatcatat ataagccaat cgcggttctt gcgattggct attttttt                   108
```

<210> SEQ ID NO 3
<211> LENGTH: 107
<212> TYPE: DNA
<213> ORGANISM: Vibrio cholerae

<400> SEQUENCE: 3
tgacccttaa ttaagccgag ggtcacctag ccaactgacg ttgttagtga atgaaattgt     60
tcacatttgt tttatcagcc aatcacccct ttgtgattgg ctttttt                  107

<210> SEQ ID NO 4
<211> LENGTH: 107
<212> TYPE: DNA
<213> ORGANISM: Vibrio cholerae

<400> SEQUENCE: 4
tgacccttct aagccgaggg tcacctagcc aactgacgtt gttagtgaac accattgttc     60
acacttatag acggccaatc acacttcttg tggttggcct ttttttt                  107

<210> SEQ ID NO 5
<211> LENGTH: 95
<212> TYPE: DNA
<213> ORGANISM: Vibrio harveyi

<400> SEQUENCE: 5 ggaccccctcg ggtcacctat ccaactgacg ttgttagtga acgacatgtt cacagaacga    60
gccaatagat ccgactgcct attggcttct ttttt                                95

<210> SEQ ID NO 6
<211> LENGTH: 109
<212> TYPE: DNA
<213> ORGANISM: Vibrio harveyi

<400> SEQUENCE: 6
cgacccttct taagccgagg gtcacctagc caactgacgt tgttagtgaa tacacattgt     60
tcacaaaata cataagccaa tcgccctaat tgcggttggc tattttttt                109

<210> SEQ ID NO 7
<211> LENGTH: 108
<212> TYPE: DNA
<213> ORGANISM: Vibrio harveyi

<400> SEQUENCE: 7
tgacccttct taagccgagg gtcacctagc caactgacgt tgttagtgga ctcgaatttg     60 ttcacaaaata tataagccaa tcgcacaaat tgcggttggc tatttttt                108

<210> SEQ ID NO 8
<211> LENGTH: 107
<212> TYPE: DNA
<213> ORGANISM: Vibrio harveyi

<400> SEQUENCE: 8
agacccttat taagccgagg gtcacctagc caactgacgt tgttagtgaa tacacattgt     60
tcacaagtat ataccgccaa tcaactttat tgtgattggc gttttttt                 107

<210> SEQ ID NO 9
<211> LENGTH: 106
<212> TYPE: DNA
<213> ORGANISM: Vibrio harveyi

<400> SEQUENCE: 9
tgaccctttt aagccgaggg tcacctagcc aactgacgtt gttagtgaac ccaattgttc    60
acacgtatat acagccaatc acaaaccttg tggttggcta tttttt                 106

<210> SEQ ID NO 10
<211> LENGTH: 95
<212> TYPE: DNA
<213> ORGANISM: Vibrio parahaemolyticus

<400> SEQUENCE: 10
cgacccctcg ggtcacctag ccaactgacg ttgttagtga acgatatgtt cacaaaacaa    60
gccaatagac ccgactgcct attggcttct ttttt                               95

<210> SEQ ID NO 11
<211> LENGTH: 108
<212> TYPE: DNA
<213> ORGANISM: Vibrio parahaemolyticus

<400> SEQUENCE: 11
cgacccttct taagccgagg gtcacctagc caactgacgt tgttagtgaa tatagattgt    60
tcacaataaa tatgagccaa tcgcgattat tgcggttggc tattttt                108

<210> SEQ ID NO 12
<211> LENGTH: 108
<212> TYPE: DNA
<213> ORGANISM: Vibrio parahaemolyticus

<400> SEQUENCE: 12
tgacccttct taagccgagg gtcacctagc caactgacgt tgttagtgaa cttgattttg    60
ttcacatgta taagccaa tcgcactctt tgcggttggc tattttt                108

<210> SEQ ID NO 13
<211> LENGTH: 107
<212> TYPE: DNA
<213> ORGANISM: Vibrio parahaemolyticus

<400> SEQUENCE: 13
tgacccttat taagccgagg gtcacctagc caactgacgt tgttagtgaa tacacattgt    60
tcacaagtat ataccgccaa tcacctttct tgtgattggc gttttt                107

<210> SEQ ID NO 14
<211> LENGTH: 107
<212> TYPE: DNA
<213> ORGANISM: Vibrio parahaemolyticus

<400> SEQUENCE: 14
tgaccctttc taagccgagg gtcacctagc caactgacgt tgttagtgaa cccaattgtt    60
cacaagtata tacagccaat cacacacctt gtggttggct ttttttt                107

<210> SEQ ID NO 15
<211> LENGTH: 93
<212> TYPE: DNA
<213> ORGANISM: Vibrio vulnificus

<400> SEQUENCE: 15 tgaccccctcg ggtcacctag ccaactgacg ttgttagtga acctagtgtt cacaattgat    60
agccaatagt gaaatgactg ttggcttttt ttt                                93

<210> SEQ ID NO 16

```
<211> LENGTH: 110
<212> TYPE: DNA
<213> ORGANISM: Vibrio vulnificus

<400> SEQUENCE: 16
cgacccttat taagccgagg gtcacctagc caactgacgt tgttagtgaa tacacattgt      60
tcacatcata cataagccaa tcgcacttat tttgcggttg gttttttttt                 110

<210> SEQ ID NO 17
<211> LENGTH: 108
<212> TYPE: DNA
<213> ORGANISM: Vibrio vulnificus

<400> SEQUENCE: 17
tgacccttat taagccgagg gtcacctagc caactgacgt tgttagtgaa cttgatttgt      60
tcacatgtat ataagccaat cgcacctttt gcggttggct cttttttt                   108

<210> SEQ ID NO 18
<211> LENGTH: 107
<212> TYPE: DNA
<213> ORGANISM: Vibrio vulnificus

<400> SEQUENCE: 18
tgacccttat taagccgagg gtcacctagc caactgacgt tgttagtgaa taatgacttg      60
ttcacacata tatacggcca aacacctgat tgtgtttggc cttttttt                   107

<210> SEQ ID NO 19
<211> LENGTH: 108
<212> TYPE: DNA
<213> ORGANISM: Vibrio vulnificus

<400> SEQUENCE: 19
tgaccctttt taagccgagg gtcacctagc caactgacgt tgttagtgaa cctgattgtt      60
cacaaatata tacagccaat cacctcttat tgtgattggc tttttttt                   108

<210> SEQ ID NO 20
<211> LENGTH: 96
<212> TYPE: RNA
<213> ORGANISM: Vibrio cholerae

<400> SEQUENCE: 20
ugacccgcaa gggucaccua gccaacugac guuguuagug aauaaucaau guucacaaau      60
aacagccaau agacucauuc uauuggcuau uuuuuu                                96

<210> SEQ ID NO 21
<211> LENGTH: 108
<212> TYPE: RNA
<213> ORGANISM: Vibrio cholerae

<400> SEQUENCE: 21
ugacccuugu uaagccgagg gucaccuagc caacugacgu uguuagugaa uaguauuguu      60
cacaucauau auaagccaau cgcgguucuu gcgauuggcu auuuuuuu                   108

<210> SEQ ID NO 22
<211> LENGTH: 107
<212> TYPE: RNA
<213> ORGANISM: Vibrio cholerae

<400> SEQUENCE: 22
ugacccuuaa uuuaagccgag ggucaccuag ccaacugacg uuguuaguga augaaauugu     60
```

-continued ucacauuugu uuuaucagcc aaucacccuu uugugauugg cuuuuuu       107

<210> SEQ ID NO 23
<211> LENGTH: 107
<212> TYPE: RNA
<213> ORGANISM: Vibrio cholerae

<400> SEQUENCE: 23
ugacccuucu aagccgaggg ucaccuagcc aacugacguu guuagugaac accauuguuc       60
acacuuauag acggccaauc acacuucuug gguuggccu uuuuuu       107

<210> SEQ ID NO 24
<211> LENGTH: 95
<212> TYPE: RNA
<213> ORGANISM: Vibrio harveyi

<400> SEQUENCE: 24
ggaccccucg ggucaccuau ccaacugacg uuguuaguga acgacauguu cacagaacga       60
gccaauagau ccgacugccu auuggcuucu uuuuu       95

<210> SEQ ID NO 25
<211> LENGTH: 109
<212> TYPE: RNA
<213> ORGANISM: Vibrio harveyi

<400> SEQUENCE: 25
cgacccuucu uaagccgagg gucaccuagc caacugacgu uguuagugaa uacacauugu       60
ucacaaaaua cauaagccaa ucgcccuaau ugcgguuggc uauuuuuuu       109

<210> SEQ ID NO 26
<211> LENGTH: 108
<212> TYPE: RNA
<213> ORGANISM: Vibrio harveyi

<400> SEQUENCE: 26
ugacccuucu uaagccgagg gucaccuagc caacugacgu uguuagugga cucgaauuug       60
uucacaaaua uauaagccaa ucgcacaaau ugcgguuggc uauuuuuu       108

<210> SEQ ID NO 27
<211> LENGTH: 107
<212> TYPE: RNA
<213> ORGANISM: Vibrio harveyi

<400> SEQUENCE: 27
agacccuuau uaagccgagg gucaccuagc caacugacgu uguuagugaa uacacauugu       60
ucacaaguau auaccgccaa ucaacuuuau ugugauuggc guuuuuu       107

<210> SEQ ID NO 28
<211> LENGTH: 106
<212> TYPE: RNA
<213> ORGANISM: Vibrio harveyi

<400> SEQUENCE: 28
ugacccuuuu aagccgaggg ucaccuagcc aacugacguu guuagugaac ccaauuguuc       60
acacguauau acagccaauc acaaaccuug gguuggcua uuuuuu       106

<210> SEQ ID NO 29
<211> LENGTH: 95
<212> TYPE: RNA

<213> ORGANISM: Vibrio parahaemolyticus

<400> SEQUENCE: 29

```
cgaccccucg ggucaccuag ccaacugacg uuguuaguga acgauauguu cacaaaacaa    60
gccaauagac ccgacugccu auuggcuucu uuuuu                               95
```

<210> SEQ ID NO 30
<211> LENGTH: 108
<212> TYPE: RNA
<213> ORGANISM: Vibrio parahaemolyticus

<400> SEQUENCE: 30

```
cgacccuucu uaagccgagg gucaccuagc caacugacgu uguuagugaa uauagauugu    60
ucacaauaaa uaugagccaa ucgcgauuau ugcgguuggc uauuuuuu               108
```

<210> SEQ ID NO 31
<211> LENGTH: 108
<212> TYPE: RNA
<213> ORGANISM: Vibrio parahaemolyticus

<400> SEQUENCE: 31

```
ugacccuucu uaagccgagg gucaccuagc caacugacgu uguuagugaa cuugauuug     60
uucacaugua uauaagccaa ucgcacucuu gcgguuggc uauuuuuu                108
```

<210> SEQ ID NO 32
<211> LENGTH: 107
<212> TYPE: RNA
<213> ORGANISM: Vibrio parahaemolyticus

<400> SEQUENCE: 32

```
ugacccuuau uaagccgagg gucaccuagc caacugacgu uguuagugaa uacacauugu    60
ucacaaguau auaccgccaa ucaccuuucu ugugauuggc guuuuuu                107
```

<210> SEQ ID NO 33
<211> LENGTH: 107
<212> TYPE: RNA
<213> ORGANISM: Vibrio parahaemolyticus

<400> SEQUENCE: 33

```
ugacccuuuc uaagccgagg gucaccuagc caacugacgu uguuagugaa cccauuguu     60
cacaaguaua uacagccaau cacacaccuu gugguuggcu uuuuuu                 107
```

<210> SEQ ID NO 34
<211> LENGTH: 93
<212> TYPE: RNA
<213> ORGANISM: Vibrio vulnificus

<400> SEQUENCE: 34

```
ugaccccucg ggucaccuag ccaacugacg uuguuaguga accuaguguu cacaauugau    60
agccaauagu gaaaugacug uuggcuuuuu uuu                                93
```

<210> SEQ ID NO 35
<211> LENGTH: 110
<212> TYPE: RNA
<213> ORGANISM: Vibrio vulnificus

<400> SEQUENCE: 35

```
cgacccuuau uaagccgagg gucaccuagc caacugacgu uguuagugaa uacacauugu    60
ucacaucaua cauuagccaa ucgcacuuau uuugcgguug guuuuuuuuu             110
```

<210> SEQ ID NO 36
<211> LENGTH: 108
<212> TYPE: RNA
<213> ORGANISM: Vibrio vulnificus

<400> SEQUENCE: 36
ugacccuuau uaagccgagg gucaccuagc caacugacgu uguuagugaa cuugauugu      60 ucacauguau auaagccaau cgcaccuuuu gcgguuggcu cuuuuuuu                 108

<210> SEQ ID NO 37
<211> LENGTH: 107
<212> TYPE: RNA
<213> ORGANISM: Vibrio vulnificus

<400> SEQUENCE: 37
ugacccuuau uaagccgagg gucaccuagc caacugacgu uguuagugaa uaaugacuug     60
uucacacaua uauacggcca aacaccugau uguguuggc cuuuuuu                   107

<210> SEQ ID NO 38
<211> LENGTH: 108
<212> TYPE: RNA
<213> ORGANISM: Vibrio vulnificus

<400> SEQUENCE: 38
ugacccuuuu uaagccgagg gucaccuagc caacugacgu uguuagugaa ccugauuguu     60
cacaaauaua uacagccaau caccucuuau ugugauuggc uuuuuuuu                 108

<210> SEQ ID NO 39
<211> LENGTH: 264
<212> TYPE: DNA
<213> ORGANISM: Vibrio harveyi

<400> SEQUENCE: 39
atggctaagg ggcaatctct acaagaccca ttcctaaatg cgctacgtcg tgagcgtatc     60
ccggtatcta tctaccttgt gaacggtatc aaactgcaag gtcagatcga atctttcgat    120
cagttcgtga tcctattgaa gaacactgtt aaccaaatgg tgtacaagca cgcaatctct    180
accgttgttc cggctcgtcc agtgagccac cacagtggtg atcgtcctca aggtgaccgt    240
ccacaagaga aatctgaaga ttaa                                           264

<210> SEQ ID NO 40
<211> LENGTH: 87
<212> TYPE: PRT
<213> ORGANISM: Vibrio harveyi

<400> SEQUENCE: 40

Met Ala Lys Gly Gln Ser Leu Gln Asp Pro Phe Leu Asn Ala Leu Arg
 1               5                  10                  15

Arg Glu Arg Ile Pro Val Ser Ile Tyr Leu Val Asn Gly Ile Lys Leu
                20                  25                  30

Gln Gly Gln Ile Glu Ser Phe Asp Gln Phe Val Ile Leu Leu Lys Asn
            35                  40                  45

Thr Val Asn Gln Met Val Tyr Lys His Ala Ile Ser Thr Val Val Pro
        50                  55                  60

Ala Arg Pro Val Ser His His Ser Gly Asp Arg Pro Gln Gly Asp Arg
 65                  70                  75                  80

Pro Gln Glu Lys Ser Glu Asp

```
<210> SEQ ID NO 41
<211> LENGTH: 264
<212> TYPE: DNA
<213> ORGANISM: Vibrio cholerae

<400> SEQUENCE: 41
atggctaagg ggcaatctct acaagaccca tttctgaatg cactacgtcg tgaacgtatc      60
cctgtttcta tctaccttgt gaacggcatt aaactgcaag gtcagatcga atcatttgat     120
caatttgtga tcttgctgaa gaacacagta accaaatgg tttacaagca tgcgatttct     180
actgtggttc ctgctcgtcc agttagccac acagcggcg accgcccagc atcggatcgt     240
ccagcagaga agtctgaaga gtaa                                             264

<210> SEQ ID NO 42
<211> LENGTH: 87
<212> TYPE: PRT
<213> ORGANISM: Vibrio cholerae

<400> SEQUENCE: 42

Met Ala Lys Gly Gln Ser Leu Gln Asp Pro Phe Leu Asn Ala Leu Arg
 1               5                  10                  15

Arg Glu Arg Ile Pro Val Ser Ile Tyr Leu Val Asn Gly Ile Lys Leu
            20                  25                  30

Gln Gly Gln Ile Glu Ser Phe Asp Gln Phe Val Ile Leu Leu Lys Asn
        35                  40                  45

Thr Val Asn Gln Met Val Tyr Lys His Ala Ile Ser Thr Val Val Pro
    50                  55                  60

Ala Arg Pro Val Ser His His Ser Gly Asp Arg Pro Ala Ser Asp Arg
65                  70                  75                  80

Pro Ala Glu Lys Ser Glu Glu
            85

<210> SEQ ID NO 43
<211> LENGTH: 16
<212> TYPE: DNA
<213> ORGANISM: Vibrio cholerae
<220> FEATURE:
<221> NAME/KEY: modified_base
<222> LOCATION: (7)..(11)
<223> OTHER INFORMATION: a, c, g, or t

<400> SEQUENCE: 43
tggcacnnnn nttgcw                                                      16

<210> SEQ ID NO 44
<211> LENGTH: 82
<212> TYPE: RNA
<213> ORGANISM: Vibrio cholerae

<400> SEQUENCE: 44
ccgaaauuca ucguuuauug uuuuauuagu aaucucguuu uacgaguuag uuguugaguu      60
aaccguuccu auauggggau ac                                               82

<210> SEQ ID NO 45
<211> LENGTH: 81
<212> TYPE: RNA
<213> ORGANISM: Vibrio harveyi

<400> SEQUENCE: 45
```

```
acgaaauucg uugauaauuu uauuaguuaa uccccugaua gggguuuuau aguugaguuu        60
accguuccuu uuaccuaaua c                                                 81

<210> SEQ ID NO 46
<211> LENGTH: 13
<212> TYPE: DNA
<213> ORGANISM: Unknown Organism
<220> FEATURE:
<223> OTHER INFORMATION: Description of Unknown Organism: Consensus
      sequence from various organisms

<400> SEQUENCE: 46
ttgcawwwtg caa                                                          13
```